United States Patent [19]
Jones et al.

[11] 4,294,824
[45] Oct. 13, 1981

[54] EXTRACTS OF THE HEMOPOIETIC SYSTEM

[75] Inventors: William A. Jones, Staines; Tse Lin Sin Tse Hing Yuen, Harpenden, both of England; Tapio Rytomaa, Helsinki, Finland; Norman J. Harper, Pyrford; Henry F. Frost, Hemel Hempstead, both of England

[73] Assignee: The Union International Company, Ltd., England

[21] Appl. No.: 917,076

[22] Filed: Jun. 19, 1978

Related U.S. Application Data

[63] Continuation-in-part of Ser. No. 667,217, Mar. 15, 1976, abandoned.

[30] Foreign Application Priority Data

Aug. 5, 1975 [GB] United Kingdom ............... 32659/75

[51] Int. Cl.$^3$ .............................................. A61K 35/14
[52] U.S. Cl. ................................................... 424/101
[58] Field of Search ......................................... 424/101

[56] References Cited

PUBLICATIONS

Rytomaa et al., Nature, vol. 222, Jun. 7, 1969, pp. 995–996.
Rytomaa et al., Europ. J. Cancer, 1970, vol. 6, pp. 401–410.

Primary Examiner—Jerome D. Goldberg
Attorney, Agent, or Firm—Jacobs & Jacobs

[57] ABSTRACT

Extracts of the hemopoietic chalones, erythrocytic, lymphocytic and granulocytic chalones are produced by the semi-continuous processing of whole blood. By means of a continuous lysis unit the red blood cells are preferentially and substantially completely lysed while leaving unaffected the leucocytes which are then separated together with the red cell debris by means of a centrifuge in which the leucocytes attach to the rotor. The intact leucocytes are extracted and the extract subjected to ultrafiltration to provide extracts of the hemopoietic chalones, which may be further isolated and purified.

Patients suffering from myeloid leukaemia have achieved temporary remissions with minimal serious or dangerous side effects when the patients received repeated doses of granulocytic chalone over an extended treatment period.

5 Claims, 10 Drawing Figures

EXTRACTS OF THE HEMOPOIETIC SYSTEM

This is a continuation-in-part of U.S. Ser. No. 667,217 filed Mar. 15, 1976 now abandoned.

The present invention relates to a process for the production of the three known chalones of the haemopoietic system, namely lymphocytic chalone, granulocytic chalone and erythrocytic chalone, from blood, and to the use of granulocytic chalone in the treatment of leukaemic conditions.

Chalones are tissue-specific, but species-unspecific, chemical inhibitors of mitosis. They are produced by the tissue upon which they act, such action possibly being the regulation of cell proliferation by a negative feedback mechanism. The possible existence of chalones has been reported in a number of systems, and in particular those from epidermis, from melanocytes, from granulocytes and from lymphocytes have been studied in some detail (T. Rytomaa, "Control of Cell Division in Mammalian Cells", Brit. Soc. for Developmental Biol. Symp. "The Cell cycle in development and differentiation" ed. Bolls and Billett, pub, Cambs. Univ. Press 1973, 457–472).

In published work on chalones it has been claimed that they are proteins or peptides, sometimes with a carbohydrate moiety, but the evidence for these claims in the case of the chalones of the haemopoietic system is very weak. Evidence for molecular size is more satisfactory, being based on physical behaviour, and all the chalones for which data have hitherto been available fall into two size groups, namely 30000–50000 daltons and 2000–5000 daltons. It is possible, and there is some evidence, that the higher molecular weight group comprises complexes of the smaller size with other substances, possibly nucleic acids or carrier proteins. Granulocytic and erythrocytic chalones are believed to belong to the 2000–5000 dalton group whereas lymphocytic chalone is believed to have a molecular size in the range 30000 to 5000 daltons. It is a very important property of chalones that their action is tissue specific but not species-specific, so that the chalones extracted from blood of any mammalian species can be applied effectively to any cell or tissue of the appropriate lineage. Granulocytic chalone can be used in the treatment of granulocytic leukaemia in man.

Both granulocytic and lymphocytic chalones have been isolated from blood serum although the actual amounts of extracts obtained are very small and these are associated with non-specific agents which may affect mitosis. Better quality material may be obtained if the leucocytes are first isolated from the blood and then extracted, although some non-specific agents are still present. Furthermore, methods employed heretofore have been batchwise processes, so that to obtain any large amount of the chalones would require a great investment in time and equipment and nothing more than laboratory-scale preparations have been carried out previously.

The separation of leucocytes from whole blood is difficult on other than a laboratory scale and no process of any kind which would be applicable to the scale of working covered by the present invention has been known heretofore. A continuous centrifuge of special design for the isolation of the formed elements of blood has been described (Tullis et al., Blood, 1952, 7 891-6, Science, 1956, 124, 792-7) but the separation of leucocytes with this is a discontinuous process in which the rotor is slowed down before the required cells emerge. Although the separated cell fraction contains 70% of the white cell (leucocyte) population, it also contains red and white cells in a ratio of 5:1 and the rate of processing is only 3 liters/hour. The NCI-IBM Continuous Flow Blood Cell Separator (Graw, Herzing et al., Transfusion, 1971, 11, 94–101) is a machine for the continuous centrifugal leucapheresis of donor blood under clinical conditions but this also has a throughput of about 3 liters/hour with average leucocyte yields of only 22%.

It is an object of the present invention to provide a process for the semi-continuous processing of whole blood to provide cellular material from which the haemopoietic chalones can be extracted on a much larger scale than previously applied.

This object is achieved according to the present process by carrying out a procedure for the extraction, separation and purification of chalones on whole blood, comprising the following steps:

(a) passing the blood, containing an anticoagulant and in the presence of a suitable lytic agent, through a continuous lysis unit under conditions such that the red blood cells present are lysed substantially completely and in preference to the leucocytes which remain substantially intact;

(b) centrifuging the lysed blood including the intact leucocytes in a manner such as to maintain the latter substantially intact while causing the leucocytes, together with stroma derived from the lysis of the red blood cells, to adhere to the rotor surface;

(c) removing the intact leucocytes and red blood cell stroma from the rotor surface while maintaining the leucocytes in a viable condition;

(d) extracting the substantially intact leucocytes together with said stroma with a suitable extractant;

(e) subjecting the extract containing granulocytic, erythrocytic and lymphocytic chalones to ultrafiltration in such a manner as to separate the granulocytic and erythrocytic chalone from the lymphocytic chalone and from other residual blood materials; and (f) recovering the lymphocytic, granulocytic and erythrocytic chalones from the respective fractions.

Further purification of the individual fractions may be carried out, for example by gel filtration, in order to provide purified chalone preparations.

The lytic agent used in step (a) is preferably hypotonic saline solution, for example of a concentration of 0.2% (W/V), although other agents such as an aqueous solution (0.83%, W/V) of ammonium chloride, or distilled water can be used. More powerful agents, such as sodium deoxycholate or saponin, are unsuitable as both red and white cells are rapidly lysed without discrimination. The lysis is preferably carried out in a delay tube, particularly one where a zone of turbulent flow occurs in the region adjacent the inlet end of the tube and where a zone of laminar flow succeeds the turbulent zone. The flow rates of blood and saline into the lysis unit are adjusted so that complete or nearly complete lysis of the red blood cells (erythrocytes) occurs during the residence time with the minimum loss of leucocytes at this stage.

In effecting centrifugation, use of a hermetically sealed clarifier (Westfalia Separators Ltd., type LG205-9, now re-designated KAI-47-525) was found to be particularly useful. The particular advantages of this machine lie in its having a design such that (a) the feedstock is admitted to the rotor without impact and turbulence and (b) the exclusion of air prevents the formation of foam. The first point is important in maintaining viability of the leucocytes, which in other types of machine tested, are damaged by the shear forces set up on impact with the rotor. On the second point, the presence of foam in the waste liquid leads to considerable losses of white cells, believed to be the result of their congregation at the air-liquid interfaces. It can be assumed that any continuous centrifuge which satsifies these additional requirements could be used in the circumstances of the present invention. The leucocytes and stroma collect as a sticky, viscous layer at the inner surfaces of the rotor and are retained there until completion of the run. It is important to this stage that the erythrocytes should be as near to completely lysed as possible in the first step, since intact erythrocytes, being more dense than leucocytes, will build up as a fluid layer next to the rotor surfaces, and would thus prevent adhesion of the leucocytes, and hence the latter will be lost in the waste liquor.

Removal of the leucocytes and stroma from the rotor is carried out in such a way that the leucocytes remain in a viable condition. This is preferably done by washing off the material adhering to the rotor with glucose saline.

Extraction of the leucocytes and red blood cell stromain stage (d) is preferably carried out with Hanks balanced salt solution (BSS) (for composition see footnote below) the cells being separated after each extraction by bucket centrifugation. The viability of the cells may be improved by the addition of glucose (0.1%, W/V) to the whole blood before lysis, and this may be advantageous with regard to the yields of active material which may be obtained.

Ultrafiltration effects fractionation of the leucocyte extracts and it has been found advantageous to use Amicon hollow-fibre cartridges and thin channel membrane systems for this operation, which is carried out at low temperatures (circa 4° C.) and preferably under aseptic conditions. The first ultrafiltration step is thus preferably carried out in an Amicon dialysis/concentration unit (type DC 2) fitted with a "Diafiber" hollow-fibre cartridge (type HDX 50) which has a nominal cut-off of 50000 daltons. The material (R-50 fraction) retained by this unit contains high molecular weight stimulators of mitosis, which may be retained or disposed of. The second step may be carried out in a similar unit fitted with a hollow-fibre cartridge (type HIDP 10) with a nominal cut-off of 10000 daltons. The sterile ultrafiltrate from the first step is processed through the second unit and the material (R-10 fraction) thereby retained (nominal molecular weight range 10000–50000 daltons) contains lymphocytic chalone and is freeze-dried before storage or further processing. The final ultrafiltration step is then advantageously performed in an Amicon thin-channel dialysis/concentration unit (type TC5B) fitted with "Diaflo" membranes (type UMO5) which have a nominal cut-off of 500 daltons. The material (R-5 fraction) retained by this unit, with a nominal molecular weight range of 500–10000 daltons, contains granulocytic and erythrocytic chalones. The freeze-dried material may then be further purified by gel filtration chromatography.

The present invention is further illustrated in the accompanying drawings, wherein.

The process will now be described in more detail below with reference particularly to an example of the extraction procedure, using ox blood, although the method has also been applied successfully to both sheep and pig blood.

Ox blood has a lymphocyte: granulocyte ratio of 3:2 with an average total white cell count of 5200 cells/mm$^3$. The best extraction results are obtained with fresh blood but good leucocyte yields can be obtained with blood which has been stored at low temperature (circa 4° C.), after the addition of a suitable anticoagulant. The anticoagulant preparation Phospro 'B' (Aldrin Products: 1.0 liter of 2.0% aq. Phospro 'B' per 10 liters of blood) has been used satisfactorily for the purpose. As stated earlier, glucose (0.1% W/V) may be added to the blood at this stage to improve cell viability, as measured by the Trypan Blue dye exclusion test (Rabinowitz, Blood, 1964, 23, 811–828; Phillips in "Tissue Culture: Methods and Applications". Ed. Kuse & Patterson, Pub. Academic Press, 1964).

Figure 1:
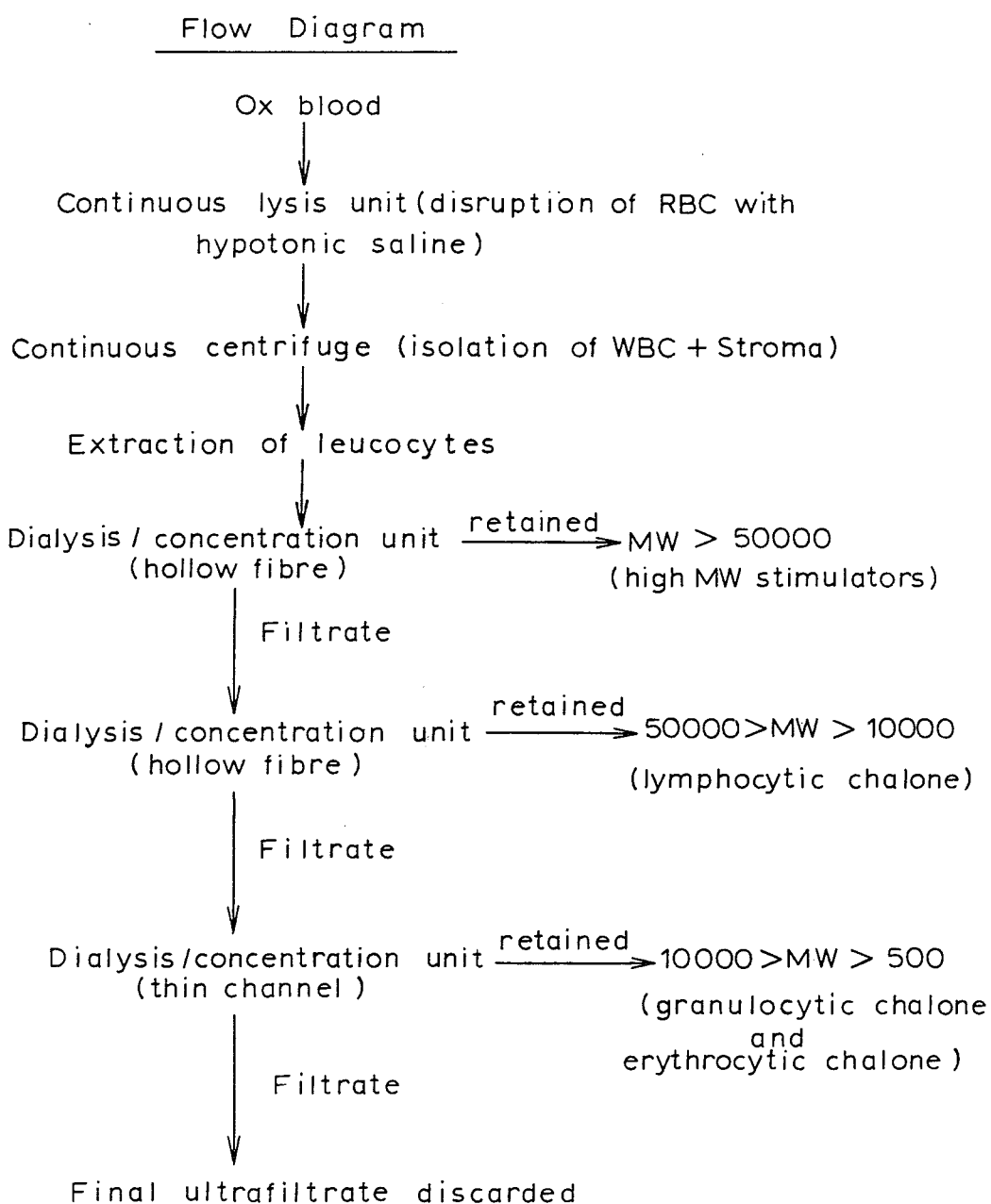
FIG. 1 is a schematic flow diagram of the process.
Figure 2:
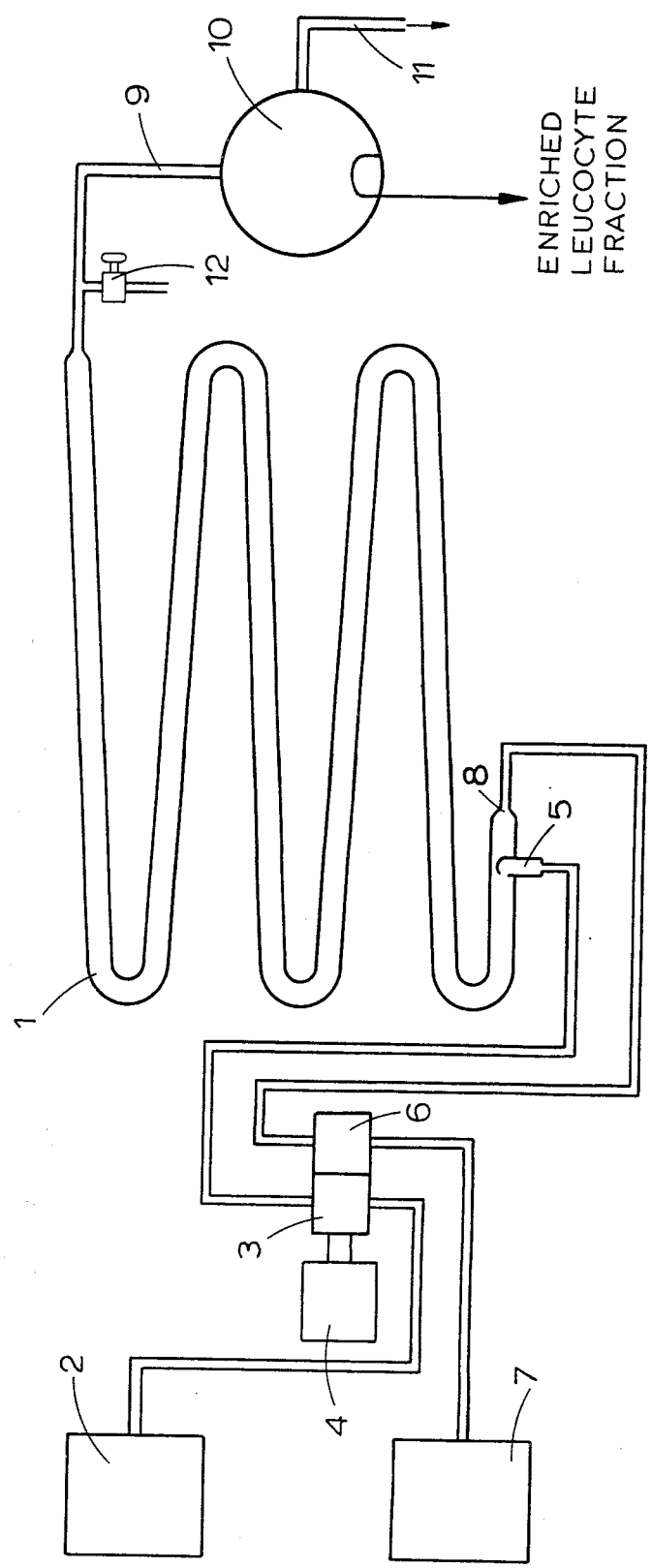
FIG. 2 shows a delay tub lysis unit of the type used in the present process.

A continuous lysis unit constructed from QVF (Jobling) glass pipe-line is shown in FIG. 2. The delay tube 1 is formed of 50 mm ID. piping, 6 m long with a volume of 12.5 l. It is fed with saline (lysis) solution source 7, through the pumphead 6 of a Normandos NP. 33 pump 4 (a micrometer—adjusted twin-headed metering pump), to the inlet 8. Blood is taken from source 2 and fed through pump 4, via head 3, to inlet 5. The mixture, after passage through the delay tube 1 is fed at inlet 9 to centrifuge 10, liquid being drawn off at outlet 11. A sampling outlet 12 is also provided in the tube.

In the present case a total flow rate of 60 liters/hr. was maintained through the delay tube giving a residence time of 12 minutes.

The whole blood (containing anticoagulant and glucose) and saline solution (sodium chloride, 0.2% W/V, in water) are fed into the lysis unit simultaneously at respective flow rate ratios of 1:4 to 1:6 controlled by the metering pump. The flow rates have to be adjusted dependent on the nature and state of the blood being processed, in order to achieve the optimum result of complete lysis of the erythrocytes with minimum loss of leucocytes. It may be advantageous to control the temperature of the lysing mixture by cooling the blood before it enters the lysis unit. The extent of lysis is most conveniently tested for by removal of a sample from the sampling cock 12 at the exit end of the lysis unit, which is then centrifuged in a graduated 10 ml conical centrifuge tube. Under conditions of inadequate lysis the intact red cells form a dark red layer at the bottom of the tube, and the flow rates are adjusted until this layer is barely detectable. Yields of approximately 60% of the total white cell population have been achieved at this stage, though accurate data are difficult to obtain owing to marked clumping of the cells recovered after centrifugation.

In the centrifugation stage, a Westfalia hermetically-sealed clarifier type LG205-9 (now known as type KAI-47-525) was used, the layer of cells being removed at the end of the run, the volume of whole blood conveniently processed in one run being approximately 45–50 liters. The run is terminated by substituting isotonic saline for blood and continuing centrifugation until the waste liquor is only slightly coloured. The cells were extracted 6 times in Hanks balanced salt solution (BSS)*, each extraction being for 1 hour at 37° C., the cells being separated after each extraction by bucket centrifugation. Inhibitory activity apparently rises to a maximum in the third or fourth extract and falls to zero in the seventh, owing to the concomitant extraction in the early stage of non-specific stimulators which offset the chalone activity in the assay system. The subsequent fall probably follows exhaustion of the chalone stores and to increasing cell death during the process.

| *Composition of Hanks balanced salt solution (BSS): is: | |
|---|---|
| Sodium chloride | 8.0 g |
| Potassium Chloride | 0.4 g |
| Magnesium Sulphate Heptahydrate | 0.2 g |
| Calcium Chloride - dihydrate | 0.185 g |
| Di-sodium Hydrogen phosphate | 0.147 g |
| Potassium Dihydrogen Phosphate | 0.060 g |
| Sodium bicarbonate | 0.35 g |
| Glucose | 1.00 g |
| Distilled water | 100 ml | pH adjusted to 7.4 with 0.1N NaOH; all reagents used of "Analar" grade.

The volume of cell extract from one day's processing was about 3 liters, but for the ultrafiltration stages, several batches of extract (say 5 or 6) were bulked to give 15–20 liters of material. Using an Amicon unit type DC2 fitted with a hollow-fibre cartridge with nominal cut-off of 50000 daltons as described above, the high molecular weight mitogens were obtained as a first fraction (R-50) in a yield of 20–30 mg/liter whole blood. In a second stage of ultrafiltration, using a similar device with a hollow-fibre cartridge with 10000 daltons cut-off, crude lymphocytic chalone (fraction R-10) was obtained in an amount of 8–13 mg/liter whole blood, while further filtration using an Amicon TC5E thin channel dialysis/concentration unit with UMO5 membranes gave the fraction (R-5) containing granulocytic and erythrocytic chalones. The final ultrafiltrate, by this stage increased in volume to about 28 liters as a result of the inclusion at each stage of the washings necessary to complete the separations, is discarded.

The freeze-dried fraction (R-5) is further purified by gel filtration column chromatography on Sephadex G-25 (Pharmacia (GB) Ltd.), by conventional procedures the eluant being 1/10 strength Hanks BSS. Granulocytic chalone has a mean $V_e/V_o$ of about 2.1, where $V_e$ is the volume of eluant necessary for the elution of the band of activity at its maximum intensity and $V_o$ is the void volume of the column, i.e., the volume of eluant in which a large molecular species which cannot penetrate the gel pores is eluted. Fractions over the $V_e/V_o$ range of 1.9 to 2.3 are collected, bulked, desalted (using the Amicon TC5E unit fitted with UMO5 membranes) and freeze-dried. The dried product is then re-assayed (by its effect on the uptake of tritiated thymidine by rat bone marrow cells), the final yield being about 140 mg/g of the R-5 fraction, i.e. about 3 mg/liter of whole blood. Further purification may be effected by a variety of methods, particularly gel filtration on a column of Sephadex G-15, polyacrylamide gel electrophoresis and iso-electric focussing.

Gel filtration using Sephadex G-15 effects the separation of pyrogenic material from the granulocytic chalone, with an approximately three-fold increase in the activity of the chalone fraction. For this stage the eluant is again 1/10 strength Hanks BSS and the granulocytic chalone is eluted between $V_e/V_o$ values of 1.45 and 1.7 whereas the pyrogenic material is eluted in the region $V_e/V_o$ 1.0–1.4. The pyrogenic contaminants are more reliably removed after the fractionation on Sephadex G-15 by first desalting the combined active fractions and then passing the retained material through a scrupulously cleaned DC2 unit with a hollow fibre cartridge of nominal 10000 daltons cut-off.

The erythrocytic chalone present may also be obtained from such a gel filtration (Sephadex G-25) process by collecting the fractions corresponding to a $V_e/V_o$ range of 2.4 to 2.6 and treating them in a manner similar to that described above for the granulocytic chalone.

A novel method for detecting erythropoietic activity was used to locate erythrocytic chalone in the column effluent and also to confirm its absence from purified granulocytic chalone preparations. The technique is based on the demonstration of reduction of DNS synthesis in the nucleated erythrocytes of the developing chick embryo, when the chalone is administered via the air sac. It was set up using erythrocytic chalone which had been extracted from washed bovine erythrocytes, and partially purified by ultra-filtration. (Krivilaakso and Rytömaa, Cell Tissue Kinet. 1971, 4, 1–9; Bateman, Cell Tissue Kinet. 1974 7 451–461).

The chalone preparations in Ringer's solution were injected during 24 hours at 4-hourly intervals and at the second chalone injection a single pulse of tritiated thymidine was given. 24 hours after the final injection, smears of blood from the dorsal aorta were prepared from control and treated embryos and autoradiographs set up. Subsequently, the proportions of red cells with labelled nuclei were determined. Although the method was not at that time capable of giving quantitative results, the results were adequate for comparative assessments. Four preparations as detailed below were tested on 6–10 eggs, each egg being injected with 0.1 ml of a 5 mg/ml solution.

| (a) | Extract of bovine erythrocytes, desalted and freeze-dried. | Significantly active |
|---|---|---|
| (b) | Sephadex G25-purified material (from bovine leucocytes) $V_e/V_o$ 1.9–2.3, desalted and freeze-dried. (granulocytic chalone) | Inactive |
| (c) | Sephadex G25-purified material (from bovine luecocytes), $V_e/V_o$ 2.4–2.6, desalted and freeze-dried. (erythrocytic chalone) | Strongly active |
| (d) | Extract of sheep leucocytes (prepared as described herein), freeze-dried. | Weakly active |

All the above preparations inhibited the uptake of tritiated thymidine by rat bone marrow cells.

Erythrocytic chalone may prove to be of use in the treatment of certain proliferative disorders of the erythron, e.g. primary and secondary (inappropriate) polycythaemia, and sideroblastic anaemia. Its value may be increased when the myeloid cell compartment is involved by administering it in conjunction with granulocytic chalone.

Further purification of the lymphocytic chalone may be effected by gel filtration chromatography on a column of Sephadex G-75 but in this case the inhibitory activity is eluted in two distinct bands, corresponding to means $V_e/V_o$ values of 1.4 to 2.4, of which only the former is specific for lymphocytes.

LYMPHOCYTIC CHALONE

Another area in which lymphocytic chalone may prove to be of therapeutic significance is organ and tissue transplantation. The major obstacle to success is rejection of the "foreign" tissue as a result of the mobilisation of the recipient's immune mechanism. This response is known to be dependent on a variety of actions of the lymphoid population and is currently controlled by the use of immunosuppressive agents. In general these are non-specific cytotoxic agents, although there is now some interest in anti-lymphocytic serum, and in anti-lymphocytic globulin isolated from such serum.

The overall intensity of the rejection phenomenon is related to the number of lymphocytes involved and any reduction of numbers of this specific population would be expected to decrease the likelihood of tissue rejection.

A method has been developed for the comparative assessment of immunosuppressive agents by their effect on the kidney allograft reaction in mice. The technique involves counting the lymphocytes which have infiltrated a specific volume of tissue immediately surrounding the allograft interface. The degree of infiltration is considered to be a measure of the immune response of the host and the ability of any agent to reduce the infiltration reflects its efficacy as an immunosuppressive drug. There is negligible lymphocytic infiltration of an isograft.

The effect of lymphocytic chalone, isolated and partially purified as described herein, has been examined by this technique. The most effective mode of administration involved perfusion of the isolated donor kidney and daily dosing of the recipient with chalone from two days prior to the transplant to 7 days after operation. This regimen produced a substantial reduction (60–70% in the numbers of lymphocytes found in the graft area.

Granulocytic chalone

Granulocytic chalone has been shown to inhibit the proliferation of normal and leukaemic granulocytic cells both in vitro and in vivo in some particular circumstances in non-human animals (Rytomaa and Kiviniemi, Cell Tissue Kinet (1968, 1, 329–350 Lacrum and Maurer, Virchows Arch. Abt. B. Zellpath 1973, 14, 293–305; Vilpo, Kiviniemi and Rytomaa, Europ. J. Cancer, 9, 515–524). Tests have been carried out on rats and mice using diffusion chambers and also it has been shown that when extracts containing granulocytic chalone are injected into rats suffering from a transplanted granulocytic leukaemia (Shay chloroleukaemia), the leukaemia regresses (Rytomaa and Kiviniemi, Nature 1969, 222, 995 and Europ. J. Cancer 1970, 6, 401–410).

Shay chloroleukaemia is an experimental condition which cannot be induced in man and its response to granulocytic chalone cannot be extrapolated to the use of granulocytic chalone in the treatment of human leukaemia.

Leukaemia is a disease characterised by abnormal widespread proliferation in bone marrow and often in other blood-forming tissues of the precursors of one of the types of leucocytes; it is of unknown causation and, within the limits of current therapeutic abilities, is uniformly fatal. Leukaemias are classified into acute or chronic, and also according to the cell type involved, e.g. granulocytic leukaemia (myeloid or myeloblastic leukaemia) involves the proliferation of the granulocytic cell line.

Recent leukokinetic studies suggest that abnormal proliferation may not provide the complete explanation of the increase in total leukocytic mass in the body in leukaemia; a decreased rate of cellular removal or destruction or a longer than normal leukocyte life span may be involved.

During the last 20 years the treatment of acute leukaemia has improved significantly particularly in the case of acute lymphocytic leukaemia in children. Better supportive care, especially through the use of platelet transfusions and more effective antimicrobial therapy has been partly responsible. Of great importance has been the development of a series of antileukaemic chemotherapeutic agents that are more toxic to leukaemic cells than to normal tissue; in most cases however the therapeutic index is narrow. Most have in common the side effect of increasing bone marrow depression and the resultant cytopenia greatly enhances the patient's susceptibility to infection, and special supportive treatment, e.g. protected patient environment and special nursing techniques, are necessary for survival. All of these chemotherapeutic agents are associated with serious side effects and toxicities: some examples are shown in Table 1, page 21.

Dosage schedules have been and continue to be manipulated in a systematic way in an attempt to determine the safest and most effective way to induce and maintain remissions. Because a combination of drugs is often better than one when none is totally effective, because mechanisms of action differ and because less toxic amounts of each might thereby be used, various combinations given together or sequentially have been tried. Examples of these are prednisone and vincristine; prednisone and 6-mercaptopurine; prednisone, vincristine and daunorubicin; prednisone, vincristine, methotrexate and 6-mercaptopurine; cystosine arabinoside and cyclophosphamide; and cyclophosphamide, vincristine, cystosine arabinose and prednisone. Combination therapy however continues to give rise to haematologic toxicity (thrombocytopenia, agranulocytosis, and anaemia) and associated problems (bleeding and infection) are considerable and not easily managed.

Drugs such as busulphan, an antineoplastic agent, are sometimes used singly in the treatment of chronic myeloid leukaemia, but again side effects are serious; in the case of busulphan the most important side effect being thrombocytopenia and haemorrhagic symptoms.

Since cure has not been achieved the search for new drugs and more effective combinations continues. In general, life is prolonged by the duration of any remission induced; in the absence of remission, little is gained by the therapy. The likelihood of inducing a remission increases if the initial treatment can be given for a minimum period of six weeks and if dosage is increased to the point of marrow depression. Consequently severe degrees of thrombocytopenia and leucopenia with the associated dangers of bleeding and infection are commonly encountered. The response of adult patients with acute myeloid leukaemia to the chemotherapeutic treatment described above is poor. Remissions occur less frequently and the tendency is to use potent and more toxic agents such as cystosine arabinoside, thioguanine and daunorobicin.

When the likelihood of a remission is low and its duration is apt to be short as in the case of myeloid leukaemia the problem is difficult and it has been argued that such patients should not be treated as a matter of routine.

Combination of cytotoxic agents with immunological therapy (BCG and X-irradiated allogeneic mycloblasts) has not been fully evaluated in the treatment of acute myeloid leukaemia and is still comparatively experimental. However it might be expected that damage to the immune system by the cytotoxic agent must to some extent limit the effectiveness of the immuno aspect of the therapy.

TABLE 1

| DRUG | SOME SIDE EFFECTS AND MAJOR TOXICITY |
| --- | --- |
| PREDNISONE | Psychosis, hypertension, peptic ulceration, fluid retention, osteoporosis, immunodepression. |
| VINCRISTINE | Peripheral neuropathy, adynamic ileus, myopathy, neutropenia, occasional thrombocytopenia, depression of haemoglobin synthesis, alopecia, paraesthesia, nausea, vomiting, psychoses. |
| DAUNORUBICIN | Myelosuppression, leucopenia, anaemia, thrombocytopenia and bleeding, nausea, vomiting, fever, alopecia, acute cardio-toxicity. |
| 6-MERCAPTOPURINE | Myelosuppression, leucopenia and thrombocytopenia with tendency to haemorrhages, hypoplasia of bone marrow, nausea, vomiting, intestinal mucositis, hepatitis. |
| METHOTREXATE | Myelosuppression, bone marrow depression, leucopenia and thrombocytopenia, intestinal mucositis, hepatitis, nausea, anorexia, vomiting, alopecia. |
| CYTOSINE ARABINOSIDE | Myelosuppression, bone marrow depression, nausea, vomiting, ulceration of mouth, conjunctivitis, lethargy and confusion. |
| CYCLOPHOSPHAMIDE | Leucopenia, anorexia, nausea, vomiting. diarrhoea, cystitis, alopecia. |

It has now been found that myeloid leukaemia in man can be treated with a surprising degree of success and without the dangerous side effects hitherto experienced in treatments of the disease. Accordingly the present invention provides a method for the treatment of patients suffering from myeloid leukaemia which comprises administering to the patients repeated doses of granulocytic chalone over an extended treatment period. The size and frequency of the doses and the extent of the treatment period will be dependent upon such factors as the stage of progress of the disease and the general medical condition of the patient.

In administering the granulocytic chalone to the patients, it is preferred to inject intravenously doses of the chalone in a suitable vehicle, but the possibility of other routes and modes of administration is not excluded. A particularly suitable chalone for administration is granulocytic chalone prepared by the methods described previously.

An elemental analysis of a sample of the granulocytic chalone of the present invention gave the following:

| | |
| --- | --- |
| Carbon | 43.6% |
| Hydrogen | 5.8% |
| Nitrogen | 6.0% |

The molecular weight is less than 1500 daltons when determined by gel techniques. While the granulocytic chalone of the present invention is sufficiently pure to produce temporary remissions with minimal serious side effects in humans with myeloid leukaemia, it may well be that the granulocytic chalone can be further purified.

By way of further description of the treatment of myeloid leukaemia in man according to the invention, a series of cases of treatment are now documented.

Seven people with diagnosed myeloid leukaemia were treated with varying doses and over varying periods with granulocytic chalone. Of these seven, 3 were cases which had previously failed to respond satisfactorily to conventional chemotherapy and in whom it might be expected that their immune system had been impaired by the cytotoxic drugs used in that therapy.

The patients all received granulocytic chalone prepared by techniques above-described from ox blood. Three batches were used and designated as OX-GC2/74, Batches 1, 2 and 3, each being obtained from approximately the same number of leucocytes. After ultrafiltration, the fraction containing the granulocytic chalone was lyophilised, further purified by gel filtration chromatography and the appropriate fractions desalted and lyophilised.

Pyrogen tests showed that all three preparations caused a febrile reaction after an i.v. injection into rabbits. 1.66 mg/kg of Batch 1 chalone, tested before the last purification step, caused an average rise of 1.0° C. in the maximum body temperature; 0.166 and 1.66 mg/kg of the Batch 2 (final) material increased body temperature by 0.8° and 1.5° C., respectively, and the corresponding doses of Batch 3, by 1.2° and 1.4° C. I.v. injections of Batch 1, before the last purification step, into rabbits for 2 weeks (from 1.66 to 8.3 mg/kg daily) caused short-term leucocytosis followed by granulocytopenia; adverse effects were not detected. Multiple i.v. injections of Batch 2 (final) material into rats up to a dose of 37.5 mg/kg were well tolerated without signs of toxicity (this dose is 25 times the highest dose given to any one of the patients).

As a result of work carried out subsequent to the clinical studies described hereinafter, it was found that further purification of the active fraction from gel filtration on Sephadex G-25 by another stage of gel filtration on Sephadex G-15 resulted in separation of the pyrogenic impurity from the chalone activity (see discussion above).

When the three preparations were tested in vitro in short term assays for biological activity on rat and human bone marrow cells in vitro in short-term assays, they were about equally active and inhibited DNA synthesis ($^3$H-TdR uptake) by 10–20% at a concentration of 10 µg/ml. Even a 100 µg/ml concentration was not cytotoxic to the cells, and affected RNA and protein syntheses (uptake of $^3$H-uridine and $^3$H-leucine, respectively) only slightly, if at all (100 μg/ml inhibited DNA synthesis by c. 50%). The Batch 1 preparation was also tested on normal human lymphocytes in vitro (20 μg/ml); it did not inhibit PHA-stimulated blastic transformation, nor did it cause chromosome damage detectable by conventional and banding techniques.

The responsiveness of each patient's leukaemic cells to the chalone was assayed in vitro. In six of the tests a single chalone pulse caused 10-30% inhibition in DNA synthesis (20 μg/ml); in the seventh the inhibition was about 5%, probably owing to poor growth of the hypoplastic bone marrow.

To obtain a better appreciation of the clinical results, the normal ranges for certain of the parameters determined in the tests, as measured in the laboratory in which testing in connection with the clinical work was done, are set out in Table 2 below. These normal ranges may be regarded as representing, "standard" data obtained under as near as possible identical conditions of testing as applied in obtaining the clinical data set out hereinafter.

TABLE 2

| Haematological and Biochemical Testing: NORMAL LABORATORY VALUES | |
|---|---|
| Parameter | Normal range for laboratory |
| Serum uric acid | 190-390 μmol/liter |
| LDH+ | 200-440 units/liter |
| Alkaline phosphatase | 60-270 units/liter |
| ASAT* | <35 units/liter |
| Creatinine | <120 μmol/liter |
| Bilirubin | <20 μmol/liter |
| Serum potassium | 3.7-4.8 mmol/liter |
| Serum sodium | 135-145 mmol/liter |
| Serum iron | 10-40 μmol/liter |
| Serum total iron - binding capacity | 54-80 μmol/liter |
| E.S.R.$^\phi$ (Westergren method) | <30 mm/hour |
| Leucocytes | 3-10 × 10$^9$ cells/liter |

+lactic acid dehydrogenase
*aspartate aminotransferase = serum glutamic oxalacetic transaminase (SGOT)
$^\phi$erythrocyte sedimentation rate The following normal values are taken from Geigy Scientific Tables, 7th edition:

| Erythrocytes | (male, 20-40 yrs) | 4.1-6.0 × 10$^{12}$ cells/liter |
| --- | --- | --- |
| | (male, >40 yrs) | 4.2-5.6 × 10$^{12}$ cells/liter |
| | (female, >40 yrs) | 4.0-5.0 × 10$^{12}$ cells/liter |
| Platelets | (venous blood) | 2.86-3.34 × 10$^{11}$ cells/liter |
| Haemoglobin | (male, 20-40 yrs) | 133-182 g/liter |
| | (male, >40 yrs) | 141-170 g/liter |
| | (female, >40 yrs) | 127-163 g/liter |
| P.C.V. | (male, 20-40 yrs) | 41-55% |
| (packed cell | (male, >40 yrs) | 41-52% |
| volume) | (female, >40 yrs) | 40-52% |

Mean differential white cell count values:

| Neutrophil granulocytes | 59% |
| --- | --- |
| Neutrophil myelocytes | 0 |
| Eosinophils | 2.4% |
| Basophils | 0.6% |
| Lymphocytes | 31% |
| Monocytes | 6.5% |

PATIENT 1

Patient 1 was a 62 year-old female who had been feeling ill since autumn 1974, and was admitted to hospital in January 1975 suffering acute abdominal pain, high fever (39°), vomiting and diarrhoea. The patient was relatively severely anaemic (85-93 g/l haemoglobin). The liver, spleen and lymph nodes were not enlarged. The patient's cardiovascular, and respiratory systems were essentially in good condition and blood pressure was normal. Gastroenteritis and a mild urinary infection (E. Coli) were diagnosed and these were treated with ampicillin (250 mg×4 daily for 2 days) and subsequently with trimethoprim plus sulphamethoxazole. As a result of a complete clinical and haematological examination acute myeloblastic leukaemia (aleukaemia) was diagnosed. Bone marrow samples from the sternum showed strong pathological myelopoiesis with numerous morphologically abnormal rapidly-proliferating granulocytes and an obvious maturation arrest.

Prior to treatment, in addition to extended clinical and laboratory examinations of a conventional nature, the patient's bone marrow cells, obtained by aspiration from the sternum, were tested in vitro for response to chalone. Two short-term experiments using microplate cultures and routine cover glass cultures indicated that incorporation of tritiated thymidine ($^3$H-TdR) into the cells was inhibited by at least 30% compared with control cultures at 20 μg/ml concentration of granulocytic chalone (Batch 1)

TREATMENT: SIDE EFFECTS 100 mg of granulocytic chalone (Batch 1) dissolved in 10 ml of physiological saline was given over 1-2 minutes by intravenous injection, twice daily for 3 days (at 11.00 hr and 20.00 hr), the dosage being reduced to 50 mg×2 daily on the fourth day. The dosage given was equivalent to approximately 1.5 mg/kg body weight. Dosage was discontinued after the fourth day, the total administered over the four days being 700 mg. Other supportive therapy during the four days consisted of phenylbutazone (i.m.), oxygen and theophylline (see Table 3).

About 40-50 minutes after the injection, the patient experienced respiratory distress (bronchospasm and increased bronchial secretion), fever, mild and irregular nausea and vomiting, these side effects persisting for about 1 hour. (All of these reactions are quite common after leukocyte transfusion). The side effects responded to the supportive therapy. When the side effects subsided the patient felt well both physically and mentally and after each administration the patient elected to continue therapy. Not unexpectedly, the patient suffered severe granulocytopenia (which substantiated the specificity of the action of granulocytic chalone). Injections were given into the same site in the vein without any sign of vascular damage. The main reason for the discontinuation of the treatment was an apparently increased risk for aspiration pneumonia: the respiratory distress tended to become stronger with time.

Details of the treatment given are shown in Table 3 below.

TABLE 3

| Treatment of Patient 1 (Chalone: Batch 1, Ox GC-2/74) | | | |
|---|---|---|---|
| Day | Dose (mg, i.v) | Max. body temperature | Supportive Treatment |
| 0 | 100 | 41.0* | None |
| | 100 | 39.5 | 600 mg PB (i.m.) |
| 1 | 100 | 37.8 | 300 mg PB (i.m.); oxygen |
| | 100 | 38.4 | " |
| 2 | 100 | 38.2 | " |
| | 100 | 38.5 | " |
| 3 | 50 | 37.7 | 300 mg PB (i.m.); |

TABLE 3-continued

Treatment of Patient 1 (Chalone: Batch 1, Ox GC-2/74)

| Day | Dose (mg, i.v) | Max. body temperature | Supportive Treatment |
|---|---|---|---|
| | 50 | | oxygen, theophylline |

Notes:
*On day 0, the "baseline" body temperature was 38.8° C. due to the gastroenteritis.
PB = phenylbutazone

Observations on Treatment

The clinical course of the disease is outlined below along with more detailed data relating to measured parameters in both tabular and graphical form.

Therapy with chalone started on day zero. After the first injection a plasma electropherogram showed increased levels of $\alpha_1$-, $\alpha_2$- and $\gamma$-globulins. On day 2 a bone marrow test showed many peroxidase positive and alkaline phosphatase positive cells. On day 3 the patient volunteered the information that she felt better, an opinion supported by the observations of the clinician in charge. During the pyrogenic reactions which followed injections there were no changes in blood pressure, no anuria and no haemolysis. The patient was given a blood transfusion of 3 units on day 9 without untoward effect and was discharged. The only medication at this stage was trimethoprim and sulphamethoxazole for the urinary tract infection.

During days 16 and 17 the patient had hospital check-ups, at which time her clinical condition was extremely good. She was ambulant and active, the improvement of the relatively severe anaemia by blood transfusion being maintained (indicating a return of the erythropoietic function of the bone marrow). There was no abnormality of the urinary sediment and a distinct improvement in serum biochemistry was noted. There were no abnormal cells in the peripheral blood and the bone marrow cytology was normal indicating that full remission had been achieved.

The patient had a further check-up on Day 31, when the clinical condition continued to be good, although there were still signs of anaemia. The blood was free from abnormal cells, granulocyte morphology was normal, but patient still showed signs of granulocytopaenia. Owing to the patient's remarkable response to chalone treatment, the correctness of the leukaemic diagnosis was questioned and suggestions made that the patient's myeloproliferative disease had been an unusual leukamoid reaction related to an undetected neoplastic tumour. This in spite of the fact that it had been made by three specialists in clinical haematology. As a consequence the patient underwent (Day 36) X-ray examination of the stomach, intestines, kidney, urinary tract, thorax and gall-bladder, none of which showed any abnormality. A liver scan and gynaecological examination were normal. The original diagnosis of acute myeloid leukaemia was confirmed. On Day 66 the patient had a further check up, when erythropoiesis appeared active. The bone marrow contained a slight excess of immature cells but these were not leukaemic. On Day 94 the patient's clinical condition remained excellent in spite of the fact that 10–15% abnormal cells had appeared in bone marrow sample and Auer bodies were detected; peripheral blood was free from abnormal cells and erythropoiesis contained to be active. A clinical relapse was expected. By Day 171 this had not materialised;—the patient's clinical condition appeared to be excellent, she was ambulant, leading an active life, no special procedure or medication were needed to protect her from infection and she was no longer anaemic. The bone marrow still contained 10–15% of abnormal cells, and peripheral blood smears showed 9% leukaemic cells.

Figure 3:
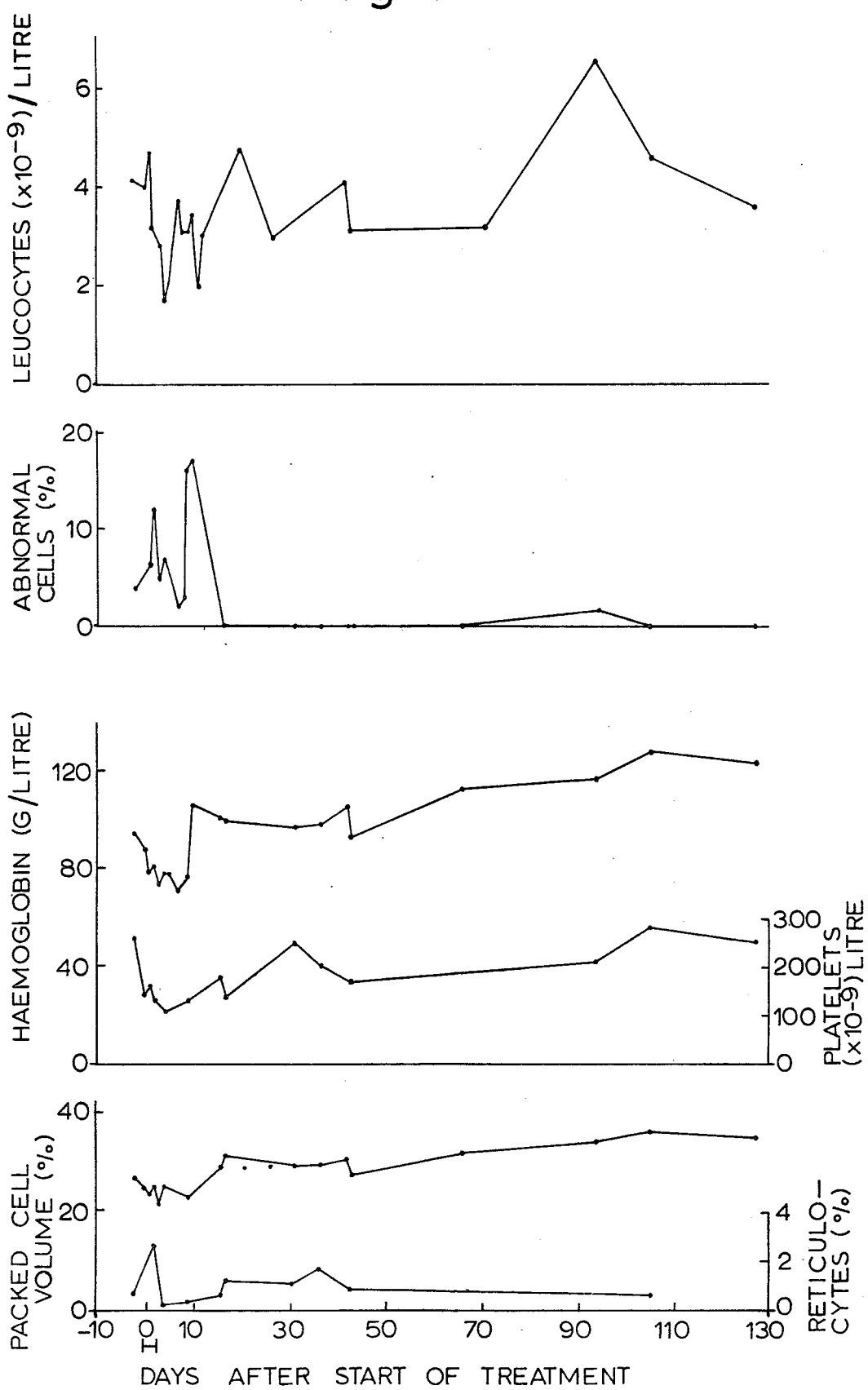
FIGS. 3 to 9 illustrate graphically the data for patients 1–7.

Biochemical and haematological data for patient 1 are given in Tables 4 to 7, following, and the data are illustrated graphically in FIG. 3.

TABLE 4

| DAY NUMBER | −2 | 0 | 1 | 2 | 3 | 4 | 5 | 6 | 7 | 8 | 9 | 10 |
|---|---|---|---|---|---|---|---|---|---|---|---|---|
| Leucocytes (Total) × 10$^{-8}$ (cells/liter) | 41.0 | 40.0 | 47.0 | 31.0 | 28.0 | 17.0 | 21.0 | | 37.0 | 31.0 | 31.0 | 34.0 |
| Lymphocytes × 10$^{-8}$ (cells/liter) | 25.0 | | 27.0 | 13.0 | 14.6 | 9.5 | | | 29.2 | 25.4 | 18.3 | 18.4 |
| Granulocytes × 10$^{-8}$ (cells/liter) | 14.6 | | 16.7 | 13.6 | 9.2 | 6.0 | | | 5.6 | 3.6 | 7.8 | 9.5 |
| Myelocytes (%) | 0 | | 0 | 0 | 0 | 0 | | | 0 | 0 | 0 | 0 |
| Metamyelocytes (%) | 1.0 | | 0 | 0 | 0 | 0 | | | 0 | 0 | 0 | 1.0 |
| Band Cells (%) | 3.0 | | 5.0 | 5.0 | 6.0 | 10.0 | | | 0 | 1.0 | 1.0 | 1.0 |
| Polymorph Neutrophils (%) | 31.0 | | 30.0 | 37.0 | 26.0 | 26.0 | | | 15.0 | 11.0 | 21.0 | 27.0 |
| Total Neutrophils (%) | 35 | | 35 | 42 | 33 | 35 | | | 15.0 | 11.5 | 22 | 28 |
| Eosinophils (%) | | | 0.5 | 1.0 | 0 | 0 | | | 0 | 0 | 3.0 | 0 |
| Basophils (%) | 0.5 | | 0 | 1.0 | 0 | 0 | | | 0 | 0 | 0 | 0 |
| Monocytes (%) | | | 0.5 | 2.0 | 2.0 | 1.0 | | | 4.0 | 3.0 | 0 | 0 |
| Leukaemic Blasts (%) | 4.0 | | 6.5 | 12.0 | 5.0 | 7.0 | | | 2.0 | 3.0 | 16.0 | 17.0 |
| Lymphocytes (%) | 61.0 | | 57.5 | 42.0 | 52.0 | 56.0 | | | 79.0 | 82.0 | 59.0 | 54.0 |
| Erythrocytes × 10$^{-12}$ (cells/liter) | 2.9 | | 2.5 | 2.7 | 2.3 | | | | | | 2.5 | |
| Reticulocytes (%) | 0.7 | | | 2.6 | | 0.2 | | | | | 0.3 | |
| Haemoglobin (g/liter) | 95 | 88 | 79 | 81 | 74 | 78 | 78 | | 71 | | 77 | 106 |
| Haematocrit (%) | 27 | 25 | 23 | 25 | 22 | 25 | | | | | 23 | |
| E.S.R. (mm/hr) | 35 | 87 | | | | 71 | | | | | 100 | |
| Platelets × 10$^{-10}$ (cells/liter) | 26 | 14 | 16 | 13 | | 11 | | | | | 13 | |
| ASAT (SGOT) (units/liter) | 29 | | | 58 | | 53 | | | 60 | | | |
| LDH (units/liter) | 580 | | | 925 | | 1045 | | | 555 | | | |
| Alkaline phosphatase (units/liter) | 405 | | | 585 | | 560 | | | 430 | | | |
| Uric Acid (μmol/liter) | | 57 | | 224 | | 126 | | | 89 | | | |
| Creatinine (μmol/liter) | 52 | | | 103 | | 103 | | | 83 | | | |
| DAY NUMBER | 16 | 17 | 31 | 36 | 37 | 42 | 43 | 66 | 94 | 105 | 127 | 171 |

TABLE 4-continued

| | 1 | 2 | 3 | 4 | 5 | 6 | 7 | 8 | 9 | 10 | 11 | 12 |
|---|---|---|---|---|---|---|---|---|---|---|---|---|
| Leucocytes (Total) × 10⁻⁸ (cells/liter) | 20.0 | 30.0 | 48.0 | 30.0 | | 41.0 | 31.0 | 32.0 | 66.0 | 46.0 | 36.0 | 37.0 |
| Lymphocytes × 10⁻⁸ (cells/liter) | 12.6 | 22.5 | 33.6 | 14.7 | | 32.4 | 21.4 | | | 28.5 | 26.6 | 24.0 |
| Granulocytes × 10⁻⁸ (cells/liter) | 7.2 | 7.4 | 14.4 | 14.7 | | 8.2 | 9.6 | | | 17.5 | 9.4 | 9.6 |
| Promyelocytes (%) | 0 | 0 | 0 | 0 | | 0 | 0 | | | 0 | 0 | 0 |
| Myelocytes (%) | 0 | 0 | 0 | 0 | | 0 | 0 | | | 0 | 0 | 0 |
| Metamyelocytes (%) | 0 | 0 | 0 | 0 | | 0 | 0 | | | 0 | 0 | 0 |
| Band Cells (%) | 2.0 | 0 | 1.0 | 0 | | 0 | 3.0 | | | 0.5 | 1.0 | 2.0 |
| Polymorph Neutrophils (%) | 37.0 | 23.0 | 29.0 | 48.0 | | 18.0 | 26.0 | | | 32.0 | 15.0 | 19.0 |
| Total Neutrophils (%) | 36 | 22.5 | 30 | 48 | | 18 | 29 | | | 33.0 | 16.0 | 21.0 |
| Eosinophils (%) | 0 | 1.0 | 0 | 1.0 | | 2.0 | 2.0 | | | 3.5 | 9.0 | 4.0 |
| Basophils (%) | 0 | 1.0 | 0 | 0 | | 0 | 0 | | | 1.5 | 1.0 | 1.0 |
| Monocytes (%) | 1.0 | 0 | 0 | 2.0 | | 1.0 | 0 | | | 0 | 0 | 0 |
| Leukaemic Blasts (%) | 0 | 0 | 0 | 0 | | 0 | 0 | 0 | 1.2 | 0 | 0 | 9.0 |
| Lymphocytes (%) | 63.0 | 75.0 | 70.0 | 49.0 | | 79.0 | 69.0 | | | 62.0 | 74.0 | 65.0 |
| Erythrocytes × 10⁻¹² (cells/liter) | 3.2 | 3.4 | 3.1 | | 3.1 | 3.3 | 2.9 | 3.7 | 3.7 | 3.9 | 4.0 | 4.0 |
| Reticulocytes (%) | 0.6 | 1.2 | 1.1 | 1.6 | | | 0.9 | | | 0.6 | | 0.8 |
| Haemoglobin (g/liter) | 101 | 100 | 97 | 99 | | 106 | 93 | 113 | 117 | 128 | 124 | 124 |
| Haematocrit (%) | 29 | 31 | 29 | 30 | | 31 | 27 | 32 | 34 | 36 | 35 | 35 |
| E.S.R. (mm/hr) | | 62 | 86 | 66 | | 55 | | 67 | | 63 | 50 | 64 |
| Platelets × 10⁻¹⁰ (cells/liter) | 18 | 14 | 25 | 20 | | | 17 | 19 | 21 | 28 | 25 | 20 |
| ASAT (SGOT) (units/liter) | | 17 | | 11 | | | | | | | 15 | 16 |
| LDH (units/liter) | | 445 | | 400 | | | | | | | 410 | 480 |
| Alkaline phosphatase (units/liter) | | 300 | | 240 | | | | | | | 405 | 380 |
| Uric Acid (μmol/liter) | | 173 | | | | | | | | | | |
| Creatinine (μmol/liter) | | 62 | | 57 | | | | | | | 68 | 58 |
| Peroxidase +ve cells (%) | | | | | | | | | | | | |
| Alkaline phosphatase (%) +ve cells | | | | | | | | | | | | |

TABLE 5

Serum Imunoglobulin Levels (g./liter) (Patient 1)

| Day No. | IgG | IgA | IgM |
|---|---|---|---|
| −2 | 14 | 2.7 | 6.5 |
| 4 | 14 | 2.7 | 5.6 |
| 17 | 19 | 3.2 | 4.2 |
| 94 | 19 | 2.6 | 3.3 |
| (normal ranges for test laboratory) | 7.0–17 | 0.7–3.5 | 0.7–3.0 |

Also tested were the proliferative activity and the cytopoietic capacity of bone marrow cell samples, taken two days before treatment started (day -2) and on day 4. For the proliferative activity test, microplate cultures are set up immediately after bone marrow sampling (BPMI 1640 essential medium supplemented with 20% of heat-inactivated AB human serum; 95% air-5% $CO_2$ atmosphere). Proliferative activity is a measure of the rate of cell production in a patient's bone marrow at the moment of sampling. The results of these tests appear in Table 6 below.

With cells taken at the same time as those for the proliferative activity tests, the cytopoietic capacity was also measured. This sample of cells was cultured for 5 days in diffusion chambers in mice, and the number of cells recovered per cell inoculated was then measured. The results are shown in Table 7 below.

TABLE 6

Proliferative Activity of Bone Marrow Cells

| Duration of test cultures (hours) | Incorporation of $^3$H-TdR 9cpm per 0.2 × 10⁶ nucleated cells; mean ± S.E. | |
|---|---|---|
| | of six cultures before treatment (day −2) | cultures taken after treatment (day 4) |
| 6 | 2706 ± 99 | 727 ± 124 |
| 24 | 4154 ± 244 | 916 ± 127 |

TABLE 7

Cytopoietic Capacity of Bone Marrow Cells

| Time of bone Marrow sampling | Number of cells recovered per cell inoculated (mean ± S.E. of 10 cultures) |
|---|---|
| day −2 | 0.42 ± 0.03 |
| day 4 | 0.44 ± 0.04 |

Commentary of Patient 1

From the haematological and biochemical data (see Tables 4, 5, 6 and 7 and FIG. 3) and from the clinical observations it is obvious that the chalone had a biological and therapeutic effect. Therapy induced changes in some haematological parameters. Chalone caused a rapid and pronounced reduction in the blood granulocyte count which decreased by approximately 65% over the 4 days of treatment, remaining below the lower limit of normal values for a considerable period of time. Even on days 16–17 the cell count remained low, returning to "normal" about Day 31.

Other cell lineages were little, if at all influenced by the therapy except blood lymphocytes (Table 4 and FIG. 3).

Prior to treatment the patient had a subleukaemic white blood cell count (3.0×10⁹ cells/liter) with 8.5% mycloblasts and 1.5% promyclocytes+myclocytes in the differential count. (A low leucocyte count is not an uncommon finding in acute myeloid leukaemia).

The blood cells classified as abnormal (FIG. 3) consisted of apparent leukaemic mycloblasts and also of cells considered to be immunoblasts on morphological grounds. Owing to the heterogeneity of this cell group, the immediate response of blood mycloblasts to chalone is not absolutely clear cut. - however in check ups on days 16, 17, 31, 36, 42 and 43, no abnormal cells of any sort were present in the differential counts. The leukaemic blasts therefore disappeared from blood at some stage after the treatment. The bone marrow morphology slowly normalised as a result of treatment. Slow changes in bone marrow cytology as opposed to rapid and direct change in blood granulocyte count are readily explained in terms of selective non-cytotoxic inhibition of granulopoiesis by excess chalone.

Despite the fact that absolute lymphocyte count never fell below the lower limit of normal values, there is evidence that the chalone treatment resulted in transient decrease in blood lymphocytes, which might have been a reflection of non-specific stress phenomena. This is supported by the rapid recovery of lymphocytes after cessation of treatment and by the persisting high amounts of circulating immunoglobulines (See Table 5). Further confirmation is provided by the fact that when OX.GC-2/74 was tested for the presence of lymphocyte chalone, the results indicated that at 20 µg/ml it had no inhibitory effect in blastic transformation of PHA-stimulated human lymphocytes.

The patient displayed severe and progressive anaemia at the onset and during the four day treatment period, the haemoglobin decreasing from Day -2 to Day 9. (Table 4, FIG. 3). The results do not clearly indicate whether decreasing haemoglobin, erythrocytes and haematocrit values were chalone induced. If there was an effect, it was at least weak and of short duration compared to the reaction of blood granulocytes. After transfusion (Day 9) the patient's haemoglobin rose as expected and remained high for an extended period. Because transfused cells have a shorter life expectancy than endogenously-produced cells, the apparent non-progression of the patient's anaemia from Day onwards demonstrates that her own erythropoiesis had improved Reticulocyte counts were all within normal limits, again indicating that the patient had active erythropoiesis.

The platelet count remained within normal limits but showed wide day to day variation (Table 4, FIG. 3).

Increases in blood uric acid levels and serum enzymes occurred and there is little doubt that therapy induced these changes, the changed values reflecting cell destruction in the leukaemic population only; i.e. destruction confined to the mycloid population.

The data (Table 6) shows that the proliferative activity of the bone marrow cells is very strongly inhibited by chalone (by more than 70%), from which it follows that as the dominating cell lineage in the patient's bone marrow was abnormal "mycloblast", this population in particular was effectively inhibited by the chalone.

The cytopoietic capacity (Table 7), which is a measure of the growth potential of bone marrow cells in a non-hostile, low-chalone environment, was not affected by the treatment indicating that the action of chalone is reversible, i.e. that the inhibited cells recovered completely when allowed to grow for a sufficiently long time in a new environment. It may also be noted that diffusion chamber cultures almost exclusively reflect the growth potential of mycloid cells (in the present case, more than 70% of the cells harvested from diffusion chambers after 5 day's culture were proliferating granulocytes, as judged from cell morphology). Because "cytopoietic capacity" was not affected by the chalone treatment, increased destruction of (leukaemic) cells must have depended on some secondary mechanism inherent to the body. It is, of course, likely that this involved the patient's immunological capacity. To some extent the conclusion is supported by the relatively high immunoglobulin content in the patient's serum (lgG on day 17) and lgM at all time points studied are higher than normal, suggesting that patient's immunological mechanism was functioning satisfactorily).

Patient 2

Patient 2 was a 66 year old male, hospitalised in the autumn of 1974 were severe respiratory distress when chronic bronchitis and emphysema were diagnosed (in 1960 patient had pulmonary tuberculosis, the apico-posterior segment of the left lung being removed). The leukocyte count was high (ca $30 \times 10^9$ cells/liter). The patient failed to respond to antibiotics and was placed in a sanatorium but no active tuberculosis was found. The leukocyte count increased steadily to $68 \times 10^9$ cells/liter. A bone marrow investigation revealed chronic mycloid leukaemia, the white blood cell count had risen to $84 \times 10^9$ cells/liter with the whole spectrum of immature and mature granulocytes in the differential count (the patient belonged to that small group of chronic granulocyte leukaemias in which granulocyte alkaline phosphatase is not pathologically low). The bone marrow aspirate was hypercellular and displayed changes typical of chronic granulocytic leukaemia—possibly already in blastic crisis. The patient's clinical condition was extremely critical, he was unable to walk unaided due to severely limited respiratory capacity and cor pulmonale, spleen and liver were enlarged extending to the umbilicus, there was ascites, axillary and inguinal lymph nodes were enlarged and thin needle biopsies from the spleen and from an inguinal node revealed myloid metaplasia.

Treatment 5 mg of granulocytic chalone dissolved in physiological saline was given over 1-2 minutes by intravenous injection four times daily for 9 days at four hourly intervals. On days 10 and 11 the dose was doubled to 10 mg ($3 \times 10$ mg on day 11). Dosage was discontinued after the 11th day, the total administered over the dosage period being 270 mg. Supportive treatment included oxygen, blood transfusions, allopurinol to control uric acid formation (See Table 8). Due to the multifaceted nature of the patient's clinical condition the patient received antibiotics (erythromycin, later ampicillin), diuretics and various symptomatic therapy.

TABLE 8

Treatment of Patient 2 with Chalone (Batch 1, Ox-GC-2/74)

| DAY | DOSE 4 hourly mg. IV. | SUPPORTIVE THERAPY | |
|---|---|---|---|
| 0 | 4 × 5 | Oxygen. | Blood Transfusion (1 unit) |
| 1 | 4 × 5 | " | " |
| 2 | 4 × 5 | " | " |
| 3 | 4 × 5 | Oxygen | |
| 4 | 4 × 5 | Oxygen. Allopurinol | Blood Transfusion (1 unit) |
| 5 | 4 × 5 | Oxygen | |
| 6 | 4 × 5 | | |
| 7 | 4 × 5 | | |

TABLE 8-continued

Treatment of Patient 2 with Chalone (Batch 1, Ox-GC-2/74)

| DAY | DOSE 4 hourly mg. IV. | SUPPORTIVE THERAPY |
|---|---|---|
| 8 | 4 × 5 | |
| 9 | 4 × 5 | |
| 10 | 4 × 10 | |
| 11 | 3 × 10 | |

The patient's clinical condition was such that he was considered to be too ill to be subjected to conventional therapy and its associated side effects. During the chalone treatment no side effects were noted (even when the dosage was doubled), apart from a slight increase in temperature (0.5° C.), which may have been associated with chalone therapy. Besides chalone, oxygen and red cell transfusions, the patient received antibiotics, diuretics (necessary despite high serum urate concentration), and various symptomatic treatment. On Day 4 allopurinol was given to control uric acid formation.

From the haematological and biochemical data (see Tables 9, 10, and FIG. 4.) and from the clinical evidence it is obvious that the chalone had a biological effect (even at dose level much lower than that given to Patient 1). Chalone administration was discontinued on Day 11 because it seemed that elimination of the large leukaemic mass was not possible without higher chalone dosage or extensively prolonged treatment period. The clinical judgement was that the patient's incurable respiratory disease and his extremely poor and weakened condition did not warrant continuation.

On Day 2 of the treatment there was a noticeable reduction in spleen size and in tenderness (the reduction was relatively small compared with that seen in the white blood cell count). Prior to treatment the patient's white cell count was high, (approximately $84 \times 10^9$ cells/liter) and rapidly increasing (of these the great majority were granulocytes). The effect of chalone was an immediate rapid and pronounced reduction in granulocyte count, other cell lineages, except blood lymphocytes were little if at all, affected. The white cell count began to decrease within 24 hours. On Day 13, 36 hours after the last dose of chalone the cell count reached a minimum after having decreased by about 75%. It can be estimated from the white cell counts that the total leukaemic mass was reduced by about 3 kg during 14 days. (This estimate is based on the assumption that in chronic granulocytic leukaemia blood counts reflect total mass of granulocytic tissue).

After Day 13 the blood count rose fairly rapidly and then appeared to enter into an oscillation with a cyclic period of about twenty days.

In this patient the absolute lymphocyte count could not be accurately determined owing to the very low relative number of lymphocytes in the differential count and to the difficulty of reliably distinguishing between lymphocytes and abnormal mycloblasts in blood smears. However, uninhibited lymphopoiesis is suggested by the persisting very high immunoglobulin content of the blood (See Table 10) and by the increasing plasma coil count in the bone marrow.

The bone marrow morphology did not change much if at all during the treatment, but plasma cell count increased with time. Bone marrow samples did not reveal signs of cytotoxicity due to chalone.

The patient showed sever anaemia before chalone treatment, but subsequently responded well to red cell transfusions, which suggested that chalone treatment neither inhibited crythropoiesis or caused haemolysis. Prior to treatment blood platelet counts were pathologically low, but abnormal bleeding was not observed. The platelet count displayed variation from day to day and appeared little if at all, affected by chalone.

It can be seen from Table 9 that changes in cellular serum enzymes especially in LDH correlate well with the rate of change in the absolute white cell count. The general pattern of change in enzyme values is similar to that seen in Patient 1, but quantitatively more marked as were the changes in uric acid levels.

It would have been unrealistic to expect a marked improvement in clincical conditions due to chalone therapy in this case, since the clinical status was dominated by the respiratory disease and cor pulmonale rather than the leukaemia.

One month after the cessation of chalone treatment the patient was transferred to a special ward for chronic malignant diseases without specific treatment. During the next month there was no progression of the leukaemia.

With time the patient became more cachectic and died on Day 68 without any sudden change in his clinical condition.

Figure 4:
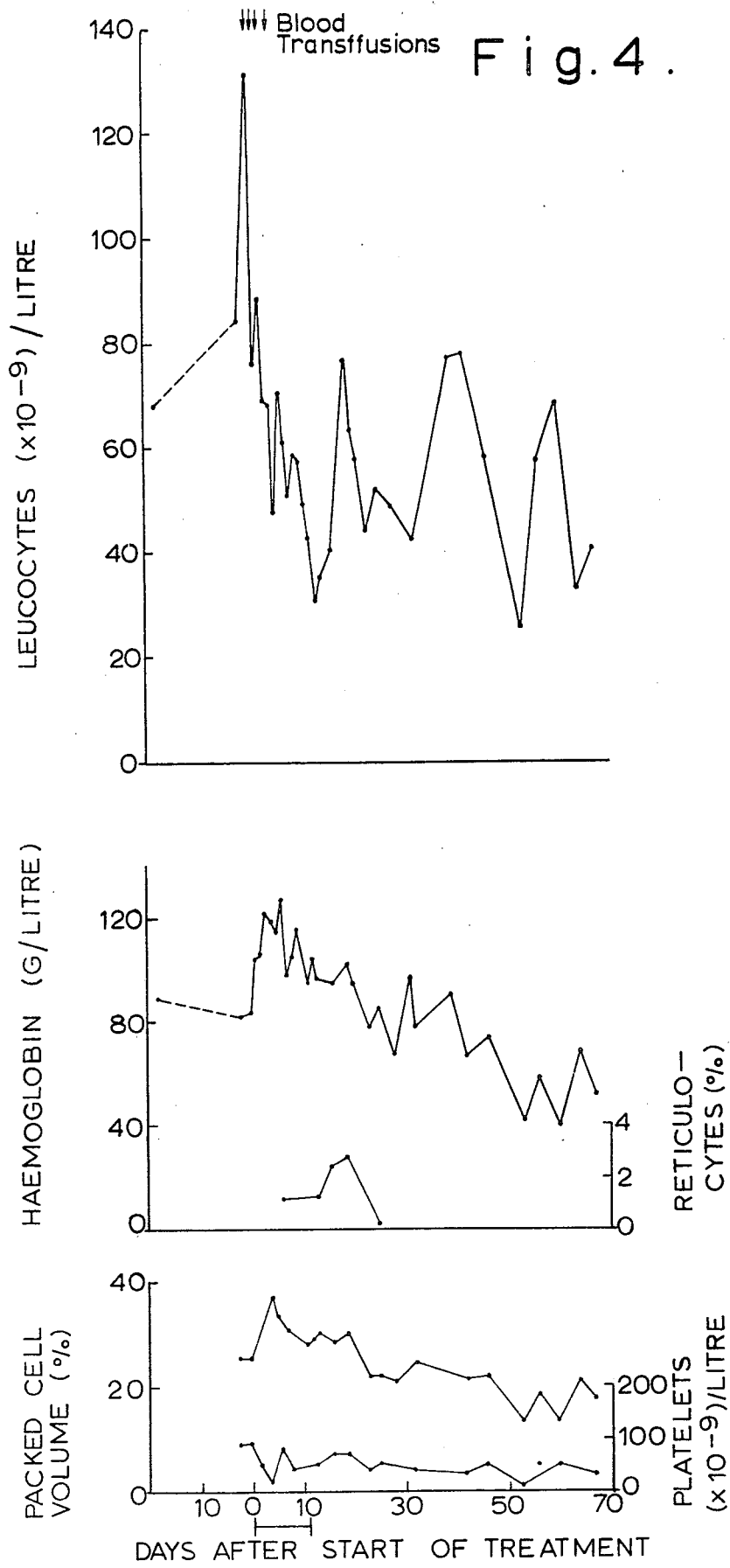

Biochemical and haematological data for Patient 2 appear below in Tables 9 and 10, and in graphical form in FIG. 4.

TABLE 9

| DAY NUMBER | −15 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|
| Leucocytes (Total) $\times 10^{-8}$ (cells/liter) | 68.0 | 84.0 | | 131.0 | 76.1 | 88.0 | 69.0 | 68.0 | 47.4 | 70.6 | 61.0 | 51.0 | 58.8 | 57.0 | 49.0 | 42.6 |
| Lymphocytes $\times 10^{-8}$ (cells/liter) | | 29.4 | | 41.9 | | 13.7 | | 27.9 | | 26.8 | | 23.0 | | | 20.8 | |
| Granulocytes $\times 10^{-8}$ (cells/liter) | | 42.0 | | 64.2 | | 47.1 | | 25.2 | | 38.1 | | 24.5 | | | 24.7 | |
| Promyelocytes (%) | | 6 | | 2 | | 1.5 | | 0.5 | | 0 | | 0 | | | 1 | |
| Myelocytes (%) | | 4 | | 5 | | 5.5 | | 2.5 | | 13 | | 3 | | | 6.5 | |
| Metamyelocytes (%) | | 16 | | 12 | | 11 | | 5.5 | | 6 | | 6 | | | 7.5 | |
| Band Cells (%) | | 6 | | 5 | | 14.5 | | 10 | | 6 | | 7 | | | 11.5 | |
| Polymorph Neutrophils (%) | | 24 | | 24 | | 22 | | 16 | | 29 | | 30 | | | 23.5 | |
| Total Neutrophils (%) | | 50 | | 46 | | 53 | | 34 | | 54 | | 46 | | | 49 | |
| Eosinophils (%) | | 0 | | 3 | | 0.5 | | 3 | | 0 | | 2 | | | 1.5 | |
| Basophils (%) | | 1 | | 0 | | 0 | | 0 | | 0 | | 0 | | | 0 | |
| Monocytes (%) | | 3 | | 12 | | 0.5 | | 7 | | 8 | | 7 | | | 2 | |
| Leukaemic Blasts (%) | | 5 | | 5 | | 29 | | 14.5 | | 0 | | 0 | | | 4 | |
| Lymphocytes (%) | | 35 | | 32 | | 15.5 | | 41 | | 38 | | 45 | | | 42.5 | |
| Erythrocytes $\times 10^{-12}$ (cells/liter) | | 2.75 | | 2.58 | | | | 3.49 | | 3.21 | | | | | | |
| Reticulocytes (%) | | | | | | | | | | 1.1 | | | | | | |
| Haemoglobin (g/liter) | 89 | 82 | | 83 | 104 | 106 | 121 | 118 | 115 | 127 | 98 | 105 | 116 | | 95 | 104 |

TABLE 9-continued

| | | | | | | | | | | | | | |
|---|---|---|---|---|---|---|---|---|---|---|---|---|---|
| Haematocrit (%) | | 25.3 | 25.4 | | | 37.0 | 33.2 | 30.3 | | 28.0 | 29.0 | | |
| E.S.R. (mm/hr) | 77 | 97 | 97 | 88 | | 75 | | | 114 | | 133 | | |
| Platelets × 10⁻¹⁰ (cells/liter) | | 90 | 90 | | 50 | 20 | | 80 | 40 | | | | |
| ASAT (SGOT) (units/liter) | | 40 | | 54 | | 105 | | | 102 | | 107 | | |
| LDH (units/liter) | | 2275 | | 2930 | | 2335 | | | 1815 | | 1775 | | |
| Alkaline phosphatase (units/liter) | | 390 | | 475 | | 1100 | | | 1330 | | 1100 | | |
| Uric Acid (μmol/liter) | | 1140 | | 1260 | | 1230 | | | 910 | | 632 | | |
| Creatinine (μmol/liter) | | 110 | | 158 | | 145 | | | 165 | | 150 | | |
| Peroxidase +ve cells (%) | | 71 | | | | 61 | | | | | 65 | | |
| Alkaline phosphatase (%) +ve cells | | 42 | | | | 41 | | | | | 45 | | |

| DAY NUMBER | 13 | 14 | 15 | 16 | 19 | 20 | 21 | 22 | 23 | 24 | 25 | 26 | 28 | 31 |
|---|---|---|---|---|---|---|---|---|---|---|---|---|---|---|
| Leucocytes (Total) × 10⁻⁸ (cells/liter) | 30.9 | 35.5 | | 40.6 | 77.0 | 63.2 | 58.0 | | 44.2 | | 51.9 | | 48.8 | |
| Lymphocytes × 10⁻⁸ (cells/liter) | 13.4 | | | 15.2 | 17.7 | | | | 18.8 | | 3.4 | | | |
| Granulocytes × 10⁻⁸ (cells/liter) | 15.6 | | | 21.1 | 43.9 | | | | 25.9 | | 22.1 | | | |
| Promyelocytes (%) | 1.5 | | | 1 | 0 | | | | 3 | | 4.5 | | | |
| Myelocytes (%) | 2.5 | | | 4.5 | 10 | | | | 7 | | 4.5 | | | |
| Metamyelocytes (%) | 6.5 | | | 10 | 10 | | | | 7 | | 12.5 | | | |
| Band Cells (%) | 12.5 | | | 18.5 | 13 | | | | 12 | | 9.5 | | | |
| Polymorph Neutrophils (%) | 27 | | | 16 | 20 | | | | 27.5 | | 13.5 | | | |
| Total Neutrophils (%) | 48.5 | | | 49 | 53 | | | | 53.5 | | 40 | | | |
| Eosinophils (%) | 1 | | | 2 | 2 | | | | 4 | | 1.5 | | | |
| Basophils (%) | 1 | | | 1 | 2 | | | | 1 | | 1 | | | |
| Monocytes (%) | 0 | | | 1 | 4 | | | | 4.5 | | 0 | | | |
| Leukaemic Blasts (%) | 45 | | | 8.5 | 16 | | | | 30 | | 46.5 | | | |
| Lymphocytes (%) | 43.5 | | | 37.5 | 23 | | | | 4 | | 6.5 | | | |
| Erythrocytes × 10⁻¹² (cells/liter) | 3.28 | | | 3.10 | | | | | 2.20 | | | | | |
| Reticulocytes (%) | 1.2 | | | 2.4 | 2.7 | | | | | | 0.2 | | | |
| Haemoglobin (g/liter) | 97 | | | 95 | 102 | 95 | | | 78 | | 85 | | 67 | 97 |
| Haematocrit (%) | 30.0 | | | 28.3 | 30.0 | | | | 22.0 | | 22.0 | | 21.0 | |
| E.S.R. (mm/hr) | | 136 | | 134 | 147 | | | | 131 | | | | 147 | |
| Platelets × 10⁻¹⁰ (cells/liter) | 50 | | | 70 | 70 | | | | 40 | | 50 | | | |
| ASAT (SGOT) (units/liter) | | | | | | | | | | | | | | |
| LDH (units/liter) | | | | | | | | | | | | | | |
| Alkaline phosphatase (units/liter) | | | | | | | | | | | | | | |
| Uric Acid (μmol/liter) | | | | | | | | | | | | | | |
| Creatinine (μmol/liter) | 152 | | | | | | | | | | 547 | | | |
| Peroxidase +ve cells (%) | | | | | | | | | | | | | | |
| Alkaline phosphatase (%) +ve cells | | | | | | | | | | | | | | |

| DAY NUMBER | 32 | 39 | 42 | 46 | 53 | 56 | 60 | 64 | 67 |
|---|---|---|---|---|---|---|---|---|---|
| Leucocytes (Total) × 10⁻⁸ (cells/liter) | 42.3 | 77.1 | 78.0 | 58.2 | 25.3 | 57.5 | 68.0 | 33.2 | 40.7 |
| Lymphocytes × 10⁻⁸ (cells/liter) | 9.7 | 5.0 | 13.3 | 0 | 1.8 | 19.6 | | 5.5 | 11.0 |
| Granulocytes × 10⁻⁸ (cells/liter) | 20.9 | 41.2 | 44.5 | 50.9 | 9.5 | 24.2 | | 19.3 | 21.2 |
| Promyelocytes (%) | 2 | 2.5 | 5 | 2 | 2.5 | 0 | | 0 | 1 |
| Myelocytes (%) | 6 | 6 | 16 | 5 | 5 | 8 | | 1.5 | 4 |
| Metamyelocytes (%) | 10.5 | 14 | 12 | 21.5 | 3.5 | 1 | | 3.5 | 1 |
| Band Cells (%) | 9 | 12.5 | 7 | 29.5 | 4.5 | 10 | | 14.5 | 9 |
| Polymorph Neutrophils (%) | 22 | 12 | 20 | 29 | 19.5 | 11 | | 30.5 | 33 |
| Total Neutrophils (%) | 475 | 44.5 | 55 | 85 | 32.5 | 30 | | 50 | 47 |
| Eosinophils (%) | 1 | 5 | 2 | 1.5 | 3.5 | 7 | | 3 | 1 |
| Basophils (%) | 1 | 4 | 0 | 1 | 1.5 | 5 | | 5 | 4 |
| Monocytes (%) | 0.5 | 2.5 | 0 | 4 | 0 | 4 | | 16.5 | 0 |
| Leukaemic Blasts (%) | 25 | 35 | 21 | 6.5 | 53 | 20 | | 9 | 20 |
| Lymphocytes (%) | 23 | 6.5 | 17 | 0 | 7 | 34 | | 16.5 | 28 |
| Erythrocytes × 10⁻¹² (cells/liter) | 2.62 | | 2.20 | 2.34 | 1.51 | 2.02 | 1.33 | 2.39 | 1.79 |
| Reticulocytes (%) | | | | | | | | | |
| Haemoglobin (g/liter) | 78 | 91 | 67 | 74 | 42 | 58 | 40 | 68 | 52 |
| Haematocrit (%) | 24.3 | | 21.2 | 21.8 | 13.3 | 18.3 | 13.7 | 21.2 | 16.9 |
| E.S.R. (mm/hr) | | | | | | | | | |
| Platelets × 10⁻¹⁰ (cells/liter) | 40 | | 30 | 50 | 10 | | 50 | | 30 |
| ASAT (SGOT) (units/liter) | 24 | | | | | | | | |
| LDH (units/liter) | 1080 | | | | | | | | |
| Alkaline phosphatase (units/liter) | 360 | | | | | | | | |
| Uric Acid (μmol/liter) | 292 | | | | | 364 | | | |
| Creatinine (μmol/liter) | 120 | | | | | | | | |

TABLE 9-continued

Peroxidase +ve cells (%)
Alkaline phosphatase (%)
+ve cells

TABLE 10

| | Serum Immunoglobulin Levels (g/liter) (Patient 2) | | |
|---|---|---|---|
| Day | IgG | IgA | IgM |
| −2 | 31 | 8.2 | 1.6 |
| 11 | 41 | 9.6 | 1.8 |
| 32 | 43 | 5.2 | 2.5 |
| (Normal ranges for the laboratory) | 7.0–17 | 0.7–3.5 | 0.7–3.0 |

Patient 3

The patient was a 31-year-old male, with two-month history of fatigue when he consulted a general practitioner, who prescribed penicillin for a sore throat. One week later, the patient was admitted to hospital in a serious condition and pneumonia was suspected. Chest X-ray showed hazy shadowing of the right lung but without typical pneumonic infiltration. Patient had high fever (39° C.), high ESR and severe anaemia (ca 60 g/liter haemoglobin), the latter not having been detected at the physical examination one week before. Leucocyte count was raised and ca 80% of these cells were abnormal mycloblast. Auer rods were present. Only 4% of the leucocytes were more mature forms of granulocytes, with virtually no polymorphs. 6.5% and less than 1% of the cells respectively were positive for peroxidase and for alkaline phosphatase. Blood platelet count was slightly subnormal. Serum LDH was raised but several other parameters were normal, including acid-base balance, serum electrolytes, thromboplastin, iron transferrin, lead, total serum proteins and urine analyses.

A bone marrow aspirate was hypercellular and showed very active, pathological, myclopoiesis. Over 90% of the cells were abnormal blasts and 18.5% were positive for peroxidase. Erythropoiesis and megakaryopoiesis were severely depressed but morphologically normal.

Spleen, liver and lymph nodes were not enlarged. Blood pressure and electrocardiogram were normal. X-ray studies of sinuses, skull, cervical spine and chest were also normal apart from the previously-mentioned shadowing of the latter. Sputum analysis failed to show the presence of pathogenic micro-organisms.

Acute myeloid leukaemia was an obvious diagnosis, which could have been made solely from examination of a peripheral blood film. The abnormality seen on the chest X-ray was possibly caused by leukaemic infiltration.

Treatment

Full details of chalone dosage and supportive treatment are given in Table 11.

From Day 3, the patient received antibiotics (tetracycline, followed by ampicillin) the latter being withdrawn on Day 13 after development of a rash which disappeared within a few days of the last dose.

Chalone treatment commenced (on Day 0) with 4 daily injections of 10 mg (c. 0.17 mg/Kg body weight) continuing until a total of 330 mg had been given (8.25 days). The injections caused a pyrogenic response on each occasion, although these were not accompanied by the respiratory distress and vomiting seen in Case 1. Increase in body temperature was controlled initially by phenylbutazone (i.m.) then by aspirin (oral) as indicated in Table 11.

For reasons described below a second course of chalone injections was commenced on Day 17, continuing until Day 39, during which time 410 mg of chalone was given, and a third course of chalone treatment was given, starting on Day 98 and running to Day 110, during which time a further 500 mg. of chalone (Batches 1 and 3) was given to the patient.

TABLE 11

Treatment of Patient 3 with Chalone (Batches 1, 2 & 3).

| DAY | CHALONE DOSAGE | SUPPORTIVE TREATMENT |
|---|---|---|
| −3 to −1 | No chalone | Tetracycline (500mg × 3) |
| 0 | 10mg × 4 (batch 1) | Phenyl butazone (200mg × 3, IM) Blood transfusion (2 u) Tetracycline (500mg × 3). |
| 1 | 10mg × 4 (batch 1) | Phenyl butazone (200mg × 3, IM) Blood transfusion (2 u) Tetracycline (500mg × 3). Aspirin (1.5g × 1, instead of phenylbutazone at evening injection. |
| 2 | 10mg × 4 (batch 1) | Aspirin (1.5g × 4) Tetracycline (500mg × 3) |
| 3 | 10mg × 4 (batch 1) | Aspirin (1.5g × 4) Tetracycline replaced by ampicillin (500mg × 4) |
| 4 to 7 | 10mg × 4 (batch 1) | Aspirin (1.5 × 4) Ampicillin (500mg × 4) |
| 8 | 10mg × 1 (batch 1) | Aspirin (1.5g × 1) Ampicillin (500mg × 4) |
| 9 | Chalone stopped | Ampicillin (500mg × 4) Blood transfusion (2 units) |
| 10 to 12 | | Ampicillin (500mg × 4) |
| 13 | | Ampicillin withdrawn |
| 17 to 22 | 10mg × 1 (batch 1) | Aspirin (1g × 1) |
| 23 | 10mg × 1 (batch 2) | No aspirin |
| 24 to 36 | 20mg × 1 (batch 2) | No aspirin |
| 37 to 39 | 30mg × 1 (batch 3) | No aspirin |
| 75 76 | | Blood transfusion (2 units) |
| 98 | 10mg × 2 (batch 1) | |
| 99 to 107 | 10mg × 4 (batch 1) | |
| 108 | 10mg × 4 (batch 3) | Blood transfusion (2 units) |
| 109 | 10mg × 4 (batch 3) | Blood transfusion (1 unit) |
| 110 | 10mg × 4 (batch 3) | |

Observations on Treatment

Figure 5:
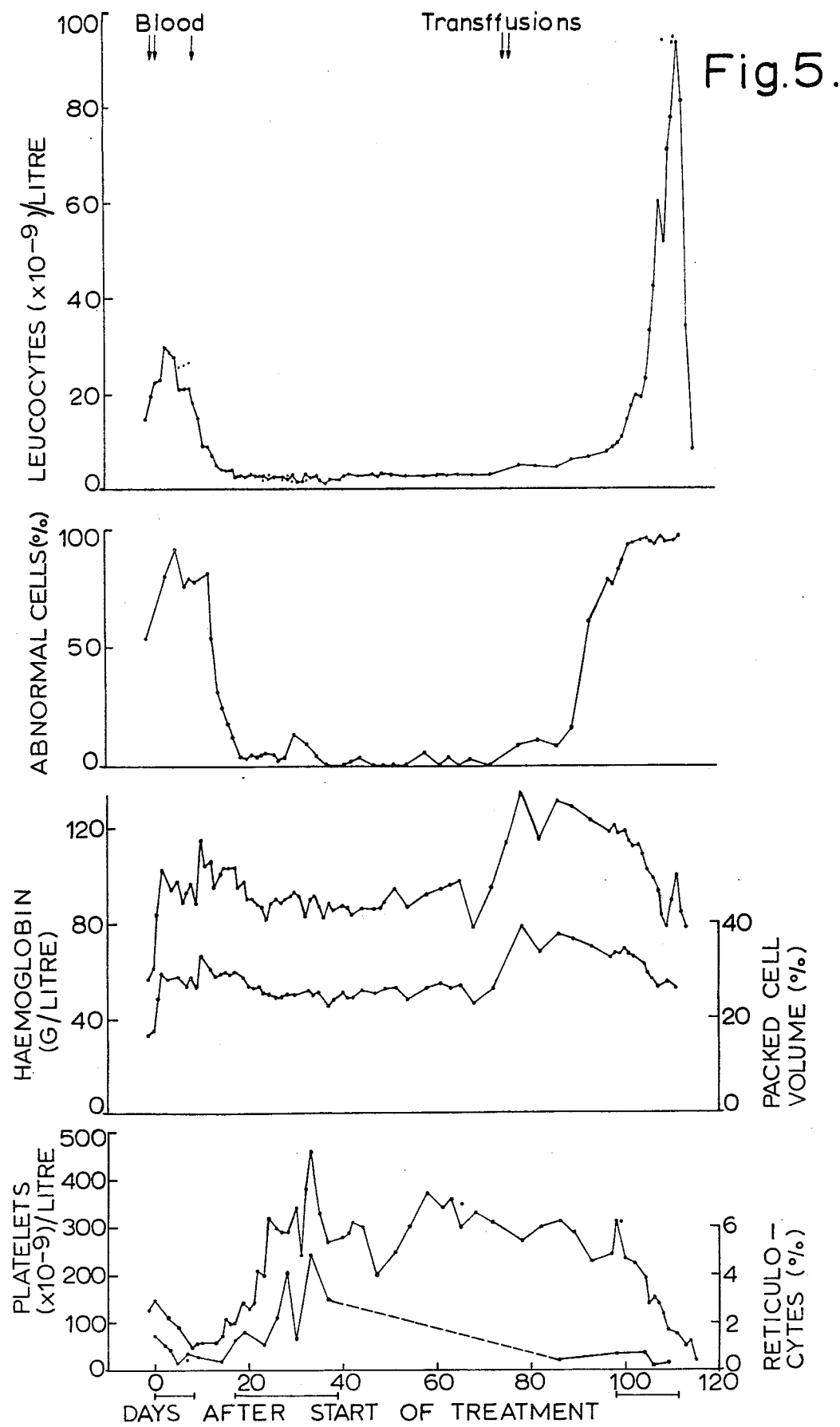

Biochemical and haematological data are given in Tables 12 and 13 and FIG. 5.

The first course of chalone injections was terminated partly because of the pyrogenic reactions and gastric irritation due to aspirin, but largely because the patient's white cell population had not by that time started to respond as expected from the experience of Cases 1 and 2. Because of this delay, and although the patient's general condition had improved considerably, he was prepared for inductive therapy.

During the next few days it became apparent that such a course was premature and that the effect of chalone had been underestimated. The leucocyte count fell from $28 \times 10^9$ cells/liter on Day 3 to $1.6 \times 10^9$ cells/liter on Day 16, the slight uptrend at c. $20 \times 10^9$ cells/liter on Days 6, 7 and 8 being mis-interpreted as a failure to respond to chalone treatment. (See Table 11 and FIG. 5). Because a bone marrow sample showed signs of re-activation of leukaemic proliferation, chalone therapy was resumed on Day 17 as a single daily injection of 10 mg, continuing until Day 39.

Leukaemic cells disappeared almost completely from the blood within 3 weeks of commencement of chalone therapy, the white cell count levelling off at c. $2 \times 10^9$ cells/liter and remaining at this for 2 months without further treatment.

As this steady state, c. 90% of the cells were lymphocytes and it can be seen from FIG. 5 that the lymphocyte population was unaffected by the chalone.

Before chalone treatment, over 90% of the bone marrow cells were leukaemic blasts; in one month the relative number of blasts decreased a 50–60% and remained at this level for the next 2 months. This high level of blasts was surprising in view of the essentially complete disappearance of leukaemic cells from peripheral blood and the remarkable improvement in the patient's general condition. Thus, although all clinical symptoms had disappeared, full remission on the basis of bone marrow examinations was not achieved. In spite of this, the marrow population of leukaemic cells remained quiescent for 2 months without artificial suppression of cell proliferation, a situation which might have continued for a longer period and been evinced to a greater degree if high doses of chalone had been continued.

The number of mature granulocytes remained very low (c. $1 \times 10^8$ cells/liter) throughout the observation period. The freedom from bacterial infection, in the absence of antibiotic cover and at a granulocyte level well below that at which it is normally considered that infection is a serious risk, is remarkable. Serum immunoglobulin levels were within normal limits (see Table 12). After discharge from hospital on Day 30, the patient lived an essentially normal working life. During this period he was engaged in manual work and was constantly exposed to microbial attack. His unexpected resistance to infection was clearly demonstrated in that the minor lacerations usually experienced in such work healed normally without signs of infection.

The severe anaemia seen on admission was substantially improved by blood transfusions during the first course of chalone treatment, the improvement being maintained for 6–7 weeks. The patient's reticulocyte and platelet counts rose 6 to 8-fold during the first and second periods of therapy, indicating that the preparation did not inhibit erythropoiesis or megakaryopoiesis. In fact, marked activation of erythrocyte and platelet production was evident in routine bone marrow samples.

Because of the marked improvement in general condition, illustrated by the patient's return to work, good appetite (resulting in a weight gain of 7 Kg) and normal sex life, further improvement of the anaemia was considered desirable, particularly as bone marrow samples revealed a complete lack of free iron. As expected, transfusions increased the haemoglobin level and haematocrit, but the improvement in the patient's general condition was relatively short-lived. After these transfusions the patient's WBC count doubled and leukaemic blasts re-appeared in the blood. Although it first seemed that the reaction was transient, full leukaemic relapse developed in a few weeks. However, there is no reason to believe that the overt disease was related to the red cell transfusions; if anything, it was triggered by a viral infection (bronchitis) which the patient had around day 80 (see Table 12) shared by other members of the household. This conclusion is supported by a previous rise in leukaemic blasts which coincided with another, milder viral infection around day 30 (see Table 12).

The patient was re-admitted to hospital on day 97 in good clinical condition but with a rapidly progressing disease. A third course of chalone treatment was started the following day, because it was now believed to be the best possible therapeutic choice (for doses, see Table 11). At first the patient responded as well as he had previously but after 6 days the leukaemia began to progress without inhibition (Table 12 and FIG. 5). Subsequent tests in vitro showed that his leukaemic populaton (bone marrow sample taken on day 111; over 90% of the cells were leukaemic blasts) did not now respond significantly to chalone (both 1st and 3rd batches) at a concentration of 20 µg/ml.

It has been reported (Roizman & Heine in "Membrane Research", ed. Fox, Pub. Academic Press, 1972, 203–237") that herpes viruses modify the nature of the surface membrane of human cells. It is possible that the diminished response of the target population at the maximum tolerated dose was the result of the chalone receptor site being altered during the viral infection and could have been overcome by the use of a larger dose of a less pyrogenic material.

The patient's general condition deteriorated rapidly during the next few weeks. It is of interest that his serum immunoglobulin values tended to decrease (Table 13) and that his resistance to bacterial infections disappeared, because on day 106 a large *S. aureus*-infected haematoma as incised from the right thigh. Drug therapy with thioguanine, daunorubicin, cytarabine, and prednisone was started on day 112, which resulted in strong pancytopenia without remission of leukaemia.

TABLE 12

| DAY NUMBER | −1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Leucocytes (Total) $\times 10^{-8}$ (cells/liter) | 145.0 | 195.0 | 220.0 | 225.0 | 290.0 | 285.0 | 271.0 | 204.0 | 209.0 | 210.0 | 180.0 | 147.0 | 89.0 | 86.0 | 69.0 | 45.0 |
| Lymphocytes $\times 10^{-8}$ (cells/liter) | 60.9 | | | 27.6 | | 17.6 | | | 37.6 | 25.2 | 34.2 | | | 13.8 | 27.9 | 27.9 |
| Granulocytes $\times 10^{-8}$ (cells/liter) | 5.8 | | | 0 | | 5.4 | | | 14.6 | 14.7 | 5.4 | | | 2.6 | 1.4 | 1.6 |
| Promyelocytes (%) | 0 | | | 11 | | 1 | | | 0 | 2 | 1 | | | 0 | 1.5 | 1.5 |
| Myelocytes (%) | 1 | | | 0 | | 0.5 | | | 2 | 2 | 2 | | | 0 | 0.5 | 0.5 |

TABLE 12-continued

| | | | | | | | | | | | | | | | |
|---|---|---|---|---|---|---|---|---|---|---|---|---|---|---|---|
| Metamyelocytes (%) | 1 | | | 0 | | 0 | | 1 | 3 | 0 | | | 0 | 0 | 1 |
| Band Cells (%) | 2 | | | 0 | | 0 | | 0 | 1 | 0 | | | 0.5 | 1 | 0 |
| Polymorph Neutrophils (%) | 0 | | | 0 | | 0.5 | | 2 | 2 | 1 | | | 2.5 | 2 | 4 |
| Total Neutrophils (%) | 4 | | | 0 | | 1 | | 5 | 8 | 3 | | | 3 | 3.5 | 5.5 |
| Eosinophils (%) | 0 | | | 0 | | 1 | | 2 | 0 | 0 | | | 1 | 0 | 0.5 |
| Basophils (%) | 0 | | | 0 | | 0 | | 0 | 0 | 0 | | | 0 | 0 | 0 |
| Monocytes (%) | 1 | | | 0 | | 0 | | 0 | 0 | 0 | | | 0 | 1 | 1 |
| Leukaemic Blasts (%) | 53 | | | 79.5 | | 90.5 | | 75 | 78 | 77 | | | 80 | 52.5 | 29.5 |
| Lymphocytes (%) | 42 | | | 9.5 | | 6.5 | | 18 | 12 | 19 | | | 16 | 40.5 | 62 |
| Erythrocytes × 10$^{-12}$ (cells/liter) | 1.7 | 1.79 | 2.52 | 3.20 | 3.10 | 3.09 | | 2.92 | 3.10 | | 3.62 | | 3.36 | 3.12 | 3.20 |
| Reticulocytes (%) | | 1.5 | | 1.1 | 0.9 | 0.3 | | 0.7 | | 0.6 | | | | | 0.4 |
| Haemoglobin (g/liter) | 57 | 62 | 84 | 103 | 100 | 95 | 98 | 89 | 93 | 97 | 89 | 115 | 107 | 106 | 95 | 101 |
| Haematocrit (%) | 16.9 | 17.7 | 24.4 | 29.6 | 28.9 | | 29.1 | | 27.0 | 28.9 | 27.0 | 33.3 | | 30.9 | 29.0 | 29.4 |
| E.S.R. (mm/hr) | 82 | 121 | 81 | 72 | | | 110 | | | 85 | | | | 33 | | |
| Platelets × 10$^{-10}$ (cells/liter) | 130 | 150 | | | 110 | | 90 | | | 50 | 60 | 60 | | | 59 | 70 |
| ASAT (SGOT) (units/liter) | | 37 | | 25 | | | 16 | | | | | | | 33 | | |
| LDH (units/liter) | | 960 | | 1440 | | | 1005 | | | | | | | 755 | | |
| Alkaline phosphatase (units/liter) | | 100 | | 205 | | | 290 | | | | | | | 200 | | |
| Uric Acid (μmol/liter) | | 177 | 359 | | | | 116 | | | | | | | | | |
| Creatinine (μmol/liter) | 92 | | | 90 | | | 93 | | | | | | | 72 | | |
| Peroxidase +ve cells (%) | 6.5 | | | | | | | | | | | | | 4.5 | | |
| Alkaline phosphatase (%) +ve cells | 1 | | | | | | | | | | | | | 1 | | |

| DAY NUMBER | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| Leucocytes (Total) × 10$^{-8}$ (cells/liter) | 39.0 | 32.0 | 34.0 | 20.0 | 24.0 | 21.0 | 26.0 | 26.0 | 27.0 | 27.0 | 14.0 | 27.0 | 25.0 | 24.0 | 20.0 | 27.0 |
| Lymphocytes × 10$^{-8}$ (cells/liter) | 28.3 | 24.2 | 28.7 | | 21.5 | 18.7 | 23.5 | 23.8 | 24.4 | 24.0 | | 22.5 | 22.9 | 19.8 | | 22.1 |
| Granulocytes × 10$^{-8}$ (cells/liter) | 1.0 | 2.1 | 1.5 | | 1.7 | 1.9 | 1.7 | 1.6 | 1.8 | 1.6 | | 3.0 | 1.9 | 3.7 | | 1.4 |
| Promyelocytes (%) | 0 | 0 | 0 | | 0 | 0 | 0 | 0 | 0 | 0 | | 0 | 0 | 0 | | 0 |
| Myelocytes (%) | 0 | 0.5 | 0 | | 0 | 0 | 0.5 | 0.5 | 0.5 | 0 | | 0 | 0 | 0 | | 1 |
| Metamyelocytes (%) | 0 | 0 | 0.5 | | 0 | 0.5 | 0 | 0 | 0 | 0 | | 0 | 0 | 0 | | 0 |
| Band Cells (%) | 0 | 0.5 | 0.5 | | 0 | 0 | 0.5 | 0 | 0 | 0 | | 0.5 | 0.5 | 0.5 | | 0 |
| Polymorph Neutrophils (%) | 2.5 | 4.5 | 3.5 | | 3.5 | 6.0 | 3.5 | 3.5 | 3.5 | 1 | | 5.5 | 4 | 7.5 | | 2 |
| Total Neutrophils (%) | 2.5 | 5.5 | 4.5 | | 3.5 | 6.5 | 4.5 | 4 | 4 | 1 | | 6 | 4.5 | 8 | | 3 |
| Eosinophils (%) | 0 | 1 | 0 | | 3.5 | 2 | 0 | 2 | 2.5 | 5 | | 5 | 3 | 7.5 | | 2 |
| Basophils (%) | 0 | 0.5 | 0 | | 0 | 0.5 | 2 | 0 | 0 | 0 | | 0 | 0 | 0 | | 0 |
| Monocytes (%) | 1 | 1 | 0 | | 0 | 0 | 0 | 0 | 0 | 1 | | 2 | 0 | 0 | | 1 |
| Leukaemic Blasts (%) | 24 | 16.5 | 11 | | 2.5 | 2 | 3 | 2.5 | 3 | 4 | | 3.5 | 1 | 2 | | 12 |
| Lymphocytes (%) | 72.5 | 75.3 | 84.5 | | 89.5 | 89.0 | 90.5 | 91.5 | 90.5 | 89 | | 83.5 | 91.5 | 82.5 | | 82.0 |
| Erythrocytes × 10$^{-12}$ (cells/liter) | 3.23 | 3.33 | 3.24 | | 3.14 | 2.91 | 2.90 | 3.03 | 2.84 | 2.80 | | 2.70 | 2.76 | 2.77 | | 2.78 |
| Reticulocytes (%) | | | 1.3 | | 1.8 | | | | 1.1 | | | 2.2 | | 4.1 | | 1.3 |
| Haemoglobin (g/liter) | 103 | 103 | 103 | 95 | | 90 | 90 | 88 | 87 | 82 | 89 | 90 | 89 | 90 | 91 | 93 |
| Haematocrit (%) | 29.8 | 29.7 | 30.0 | | 28.6 | 26.4 | 26.2 | 26.9 | 25.6 | 25.2 | | 24.5 | 24.9 | 25.0 | | 24.9 |
| E.S.R. (mm/hr) | | 29 | | | 30 | | | | | | | 25 | | | | |
| Platelets × 10$^{-10}$ (cells/liter) | 108 | 100 | | | 140 | 130 | 140 | 210 | 200 | 230 | | 300 | 290 | 290 | | 340 |
| ASAT (SGOT) (units/liter) | | | | | 22 | | | | | | | 16 | | | | |
| LDH (units/liter) | | | | | 565 | | | | | | | 545 | | | | |
| Alkaline phosphatase (units/liter) | | | | | 160 | | | | | | | 150 | | | | |
| Uric Acid (μmol/liter) | | | | | 320 | | | | | | | 310 | | | | |
| Creatinine (μmol/liter) | | | | | 80 | | | | | | | | | | | |
| Peroxidase +ve cells (%) | | | | | | | | | 3.5 | | | | | | | |
| Alkaline phosphatase (%) +ve cells | | | | | | | | | 2.5 | | | | | | | |

| DAY NUMBER | 31 | 32 | 33 | 34 | 35 | 36 | 37 | 38 | 39 | 40 | 41 | 42 | 4 | 7 | 8 | 9 |
|---|---|---|---|---|---|---|---|---|---|---|---|---|---|---|---|---|
| Leucocytes (Total) × 10$^{-8}$ (cells/liter) | 14. | 15.0 | 29.0 | 21.0 | 24.0 | 13.0 | 10.0 | 15.0 | | 16.0 | 25.0 | 29.0 | 28.0 | 29.0 | 23.0 | 25.0 |
| Lymphocytes × 10$^{-8}$ (cells/liter) | | | 24.1 | | 21.5 | | 9.1 | | | | 22.3 | 25.8 | 23.8 | 26.4 | | 22.9 |
| Granulocytes × 10$^{-8}$ (cells/liter) | | | 2.6 | | 1.8 | | 0.9 | | | | 2.5 | 2.9 | 3.4 | 2.6 | | 2.1 |
| Promyelocytes (%) | | | 0 | | 0 | | 0 | | | | 0 | 0 | 0 | 0 | | 0 |
| Myelocytes (%) | | | 0 | | 0 | | 0 | | | | 0 | 0 | 0 | 0 | | 0 |
| Metamyelocytes (%) | | | 0 | | 0 | | 0 | | | | 0 | 0 | 0 | 0 | | 0 |
| Band Cells (%) | | | 0 | | 1 | | 0 | | | | 0 | 0 | 1 | 0 | | 1 |
| Polymorph Neutrophils (%) | | | 4 | | 4.5 | | 3.5 | | | | 5 | 4 | 7 | 5 | | 6 |
| Total Neutrophils (%) | | | 4 | | 5.5 | | 3.5 | | | | 5 | 4 | 8 | 5 | | 7 |
| Eosinophils (%) | | | 5 | | 1.5 | | 4.5 | | | | 5 | 6 | 4 | 4 | | 1.5 |
| Basophils (%) | | | 0 | | 0.5 | | 0.5 | | | | 0 | 0 | 0 | 0 | | 0 |
| Monocytes (%) | | | 0 | | 0 | | 0.5 | | | | 1 | 0 | 0 | 0 | | 0 |
| Leukaemic Blasts (%) | | | 8 | | 3 | | 0 | | | | 0 | 1 | 3 | 0 | | 0 |
| Lymphocytes (%) | | | 83.0 | | 89.5 | | 91.0 | | | | 89 | 89 | 85 | 91 | | 91.5 |
| Erythrocytes | | | | | | | | | | | | | | | | |

TABLE 12-continued

| | | | | | | | | | | | | | | | |
|---|---|---|---|---|---|---|---|---|---|---|---|---|---|---|---|
| × 10⁻¹² (cells/liter) | | | 2.82 | | 2.79 | | 2.45 | 2.57 | | 2.72 | 2.72 | 2.61 | | 2.71 | 2.85 |
| Reticulocytes (%) | | | 4.8 | | | | 3.0 | | | | | | | | |
| Haemoglobin (g/liter) | 91 | 83 | 90 | 91 | 87 | 82 | 88 | 85 | | 87 | 86 | 83 | 26.0 | 25.2 | 26.5 |
| Haematocrit (%) | | | 26.0 | 25.0 | 25.6 | | 22.7 | 24.1 | | 25.9 | 24.7 | 24.2 | 26.0 | 25.2 | 26.5 |
| E.S.R. (mm/hr) | | | | | | | 53 | | | | | | | 29 | |
| Platelets × 10⁻¹⁰ (cells/liter) | 240 | 380 | 460 | | 330 | | 270 | | | 280 | 290 | 310 | 300 | 200 | |
| ASAT (SGOT) (units/liter) | | | | | | | 15 | | | | | | | 19 | |
| LDH (units/liter) | | | | | | | 575 | | | | | | | 640 | |
| Alkaline phosphatase (units/liter) | | | | | | | 140 | | | | | | | 140 | |
| Uric Acid (μmol/liter) | | | | | | | | | | | | | | 344 | |
| Creatinine (μmol/liter) | | | | | | | 88 | | | | | | | | |
| Peroxidase +ve cells (%) | | | | | | | | | | | | | | | |
| Alkaline phosphatase (%) +ve cells | | | | | | | | | | | | | | | |

| DAY NUMBER | 4 | 8 | | 63 | 65 | 68 | 72 | 78 | 82 | 86 | 89 | 93 | 97 | 98 | 99 |
|---|---|---|---|---|---|---|---|---|---|---|---|---|---|---|---|
| Leucocytes (Total) × 10⁻⁸ (cells/liter) | 25.0 | 23.0 | 25.0 | 26.0 | 23.0 | 26.0 | 23.0 | 28.0 | 48.0 | 46 | 44 | 58 | 64 | 78 | 86 | 91 |
| Lymphocytes × 10⁻⁸ (cells/liter) | 24.0 | 21.2 | 24.1 | 23.9 | 20.4 | 23.3 | 21.2 | 27.0 | 41.3 | 39.1 | 38.7 | 48.7 | 24.3 | 14.8 | 18.9 | 14.6 |
| Granulocytes × 10⁻⁸ (cells/liter) | 2.0 | 1.8 | 0.8 | 1.8 | 1.8 | 2.7 | 0.9 | 1.0 | 2.4 | 2.3 | 1.8 | 0.6 | 1.9 | 2.3 | 1.7 | 1.8 |
| Promyelocytes (%) | 0 | 0 | 0 | 0 | 0 | 0 | 0 | 0 | 0 | 0 | 0 | 0 | 0 | 0 | 0 | 0 |
| Myelocytes (%) | 0 | 0 | 0 | 0 | 0 | 0 | 0 | 0.5 | 1 | 0 | 0 | 0 | 0 | 0 | 0 | 0.5 |
| Metamyelocytes (%) | 0 | 0 | 0 | 0 | 0 | 0 | 0 | 0 | 0 | 0 | 0 | 0 | 0 | 0.5 | 0 | 0 |
| Band Cells (%) | 0 | 0 | 0 | 0 | 0 | 0 | 0 | 0 | 0 | 0 | 0 | 0 | 0 | 0.5 | 0.5 | 0 |
| Polymorph Neutrophils (%) | 2 | 8 | 2 | 5 | 6 | 4.5 | 2.0 | 2.5 | 1 | 4 | 2 | 1 | 0.5 | 0 | 0 | 0.5 |
| Total Neutrophils (%) | 2 | 8 | 2 | 5 | 6 | 4.5 | 2.0 | 3.0 | 2.0 | 4.0 | 2.0 | 1.0 | 0.5 | 1.0 | 0.5 | 1.0 |
| Eosinophils (%) | 2 | 0 | 1 | 2 | 2 | 6 | 2 | 0 | 3 | 1 | 2 | 0 | 1.5 | 2 | 1 | 0.5 |
| Basophils (%) | 0 | 0 | 0 | 0 | 0 | 0 | 0 | 0 | 0 | 0 | 0 | 0 | 0 | 0 | 0.5 | 0.5 |
| Monocytes (%) | 0 | 0 | 0 | 0 | 0 | 0 | 0 | 0 | 1 | 0 | 0 | 0 | 0 | 0 | 0 | 0 |
| Leukaemic Blasts (%) | 0 | 0 | 5 | 0 | 3.5 | 0 | 0 | 0 | 8 | 10 | 8 | 15 | 60 | 78 | 76 | 82 |
| Lymphocytes (%) | 96.0 | 92.0 | 96.5 | 92.0 | 88.5 | 89.5 | 92.0 | 96.5 | 86.0 | 85 | 88 | 84 | 38 | 19 | 22 | 16 |
| Erythrocytes × 10⁻¹² (cells/liter) | 2.85 | 2.53 | 2.76 | 2.82 | 2.84 | 2.85 | 2.33 | 2.74 | 4.25 | 4.23 | 4.02 | 3.89 | 3.90 | 3.63 | 3.75 | 3.70 |
| Reticulocytes (%) | | | | | | | | | | | 0.4 | | | | 0.7 | |
| Haemoglobin (g/liter) | 94 | 87 | 92 | 94 | 96 | 97 | 78 | 94 | 134 | 115 | 131 | 128 | 123 | 118 | 121 | 117 |
| Haematocrit (%) | 26.6 | 24.0 | 26.5 | 27.2 | 26.2 | 26.9 | 23.1 | 26.0 | 39.4 | 34.0 | 37.4 | 35.8 | 35.0 | 32.9 | 33.9 | 33.8 |
| E.S.R. (mm/hr) | | | | 14 | | 13 | 12 | 21 | | | 10 | | | | 7 | |
| Platelets × 10⁻¹⁰ (cells/liter) | 245 | 300 | 370 | 340 | 360 | 300 | 330 | 310 | 270 | 300 | 310 | 290 | 230 | 240 | 310 | |
| ASAT (SGOT) (units/liter) | | | | | | | 21 | | | | 21 | | | | 24 | |
| LDH (units/liter) | | | | | | | 635 | | | | 870 | | | | 790 | |
| Alkaline phosphatase (units/liter) | | | | | | | 155 | | | | 160 | | | | 175 | |
| Uric Acid (μmol/liter) | | | | | | | | | | | 344 | | | | 322 | |
| Creatinine (μmol/liter) | | | | | | | | | | | 85 | | | | 85 | |
| Peroxidase +ve cells (%) | | | | | | | | | | | | | | | | |
| Alkaline phosphatase (%) +ve cells | | | | | | | | | | | | | | | | |

| DAY NUMBER | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|
| Leucocytes (Total) × 10⁻⁸ (cells/liter) | 105 | 145 | 172 | 195 | 190 | 223 | 332 | 420 | 600 | 521 | 710 | 778 | 930 | 810 | 340 | 81 |
| Lymphocytes × 10⁻⁸ (cells/liter) | 13.7 | 10.9 | 10.3 | | 10.5 | 8.9 | 11.6 | 16.8 | 21.0 | 23.4 | | 23.3 | 23.3 | 52.7 | 23.8 | 13.0 |
| Granulocytes × 10⁻⁸ (cells/liter) | 1.1 | 0 | 1.7 | | 0 | 2.2 | 8.3 | 4.2 | 3.0 | 0 | | 7.8 | 9.3 | 8.1 | 1.7 | 1.6 |
| Promyelocytes (%) | 0 | 0 | 0 | | 0 | 0 | 0 | 1 | 0.5 | 1.5 | | .1 | 0.5 | 1.5 | 0.5 | 1.5 |
| Myelocytes (%) | 0 | 0 | 0 | | 0 | 0 | 1.5 | 0 | 0.5 | 0 | | 0 | 0 | 0 | 0 | 0 |
| Metamyelocytes (%) | 0 | 0 | 0 | | 0 | 0 | 0 | 0 | 0 | 0 | | 0 | 0 | 0 | 0 | 0 |
| Band Cells (%) | 0.5 | 0 | 0 | | 0 | 0 | 0.5 | 0 | 0 | 0 | | 0 | 0 | 0.5 | 0 | 0.5 |
| Polymorph Neutrophils (%) | 0 | 0 | 1 | | 0 | 0.5 | 0 | 0.5 | 0 | 0 | | 0.5 | 0.5 | 0 | 0 | 1.5 |
| Total Neutrophils (%) | 0.5 | 0 | 1.0 | | 0 | 0.5 | 2.0 | 0.5 | 0.5 | 0 | | 0.5 | 0.5 | 0.5 | 0 | 2.0 |
| Eosinophils (%) | 0.5 | 0 | 0 | | 0 | 0.5 | 0.5 | 0.5 | 0 | 0 | | 0 | 0.5 | 0.5 | 0.5 | 0 |
| Basophils (%) | 0 | 0 | 0 | | 0 | 0 | 0 | 0 | 0 | 0 | | 0.5 | 0 | 0 | 0 | 0 |
| Monocytes (%) | 0 | 0 | 0 | | 0 | 0 | 0 | 0 | 0 | 0 | | 0 | 0 | 0 | 0 | 0 |
| Leukaemic Blasts (%) | 86 | 92.5 | 93 | | 94.5 | 95 | 94 | 94 | 95.5 | 94 | | 95 | 96 | 91 | 92 | 80.5 |
| Lymphocytes (%) | 13 | 7.5 | 6 | | 5.5 | 4.0 | 3.5 | 4.0 | 3.5 | 4.5 | | 3.0 | 2.5 | 6.5 | 7 | 16 |
| Erythrocytes × 10⁻¹² (cells/liter) | 3.66 | 3.59 | 3.53 | | 3.35 | 3.17 | 3.03 | 2.85 | 2.46 | | | | | | 3.08 | 3.64 |
| Reticulocytes (%) | | | | | | 0.7 | | 0.2 | | 0.3 | | | | | | 0.1 |
| Haemoglobin (g/liter) | 118 | 114 | 112 | 112 | 109 | 102 | 99 | 93 | 79 | 89 | 100 | 84 | 79 | 98 | | 94 |
| Haematocrit (%) | 34.2 | 33.9 | 32.9 | | 31.1 | 29.6 | 28.4 | 26.5 | 23.7 | 28.0 | | 27.0 | | | | 27.0 |
| E.S.R. (mm/hr) | | | | | | 48 | | | | 72 | | | | | | |
| Platelets × 10⁻¹⁰ (cells/liter) | 230 | | 220 | | 190 | 140 | 150 | 140 | 120 | 90 | | 80 | 60 | 50 | 60 | 20 |
| ASAT (SGOT) (units/liter) | | | | | 15 | | | | | | | | | | | |
| LDH (units/liter) | | | | | 725 | | | | | | | | | | | |
| Alkaline phosphatase | | | | | | | | | | | | | | | | |

TABLE 12-continued

| | | |
|---|---|---|
| (units/liter) | | |
| Uric Acid (μmol/liter) | 240 | 105 |
| Creatinine (μmol/liter) | 344 | |
| Peroxidase +ve cells (%) | 93 | |
| Alkaline phosphatase (%) +ve cells | | |

| DAY NUMBER | 116 | 118 | 119 |
|---|---|---|---|
| Leucocytes (Total) × $10^{-8}$ (cells/liter) | 37 | 17 | 12 |
| Lymphocytes × $10^{-8}$ (cells/liter) | | 9.2 | 8.6 |
| Granulocytes × $10^{-8}$ (cells/liter) | | 0.5 | 0.4 |
| Promyelocytes (%) | | 0 | 0 |
| Myelocytes (%) | | 0 | 0 |
| Metamyelocytes (%) | | 0 | 0 |
| Band Cells (%) | | 2 | 2 |
| Polymorph Neutrophils (%) | | 1 | 0 |
| Total Neutrophils (%) | | 3.0 | 2.0 |
| Eosinophils (%) | | 0 | 1 |
| Basophils (%) | | 0 | 0 |
| Monocytes (%) | | 0 | 0 |
| Leukaemic Blasts (%) | | 43 | 25 |
| Lymphocytes (%) | | 54 | 72 |
| Erythrocytes × $10^{-12}$ (cells/liter) | | 3.43 | 3.16 |
| Reticulocytes (%) | | | |
| Haemoglobin (g/liter) | 109 | 99 | 91 |
| Haematocrit (%) | 31.4 | 29.4 | 27.1 |
| E.S.R. (mm/hr) | | | |
| Platelets × $10^{-10}$ (cells/liter) | 30 | 20 | 10 |
| ASAT (SGOT) (units/liter) | | | |
| LDH (units/liter) | | | |
| Alkaline phosphatase (units/liter) | | | |
| Uric Acid (μmol/liter) | | | |
| Creatinine (μmol/liter) | | | |
| Peroxidase +ve cells (%) | | | |
| Alkaline phosphatase (%) +ve cells | | | |

TABLE 13

Serum Immunoglobulin Levels (g/liter) Patient 3

| Day | IgG | IgA | IgM |
|---|---|---|---|
| 1 | 8.7 | 2.2 | 0.6 |
| 5 | 8.6 | 2.3 | 0.5 |
| 26 | 9.7 | 2.5 | 0.8 |
| 37 | 12 | 2.5 | 0.9 |
| 47 | 12 | 2.3 | 1.0 |
| 68 | 12 | 2.4 | 0.7 |
| 86 | 12 | 2.3 | 0.9 |
| 104 | 11 | 1.8 | 0.7 |
| (normal ranges for the test laboratory) | 7.0–17 | 0.7–3.5 | 0.7–3.0 |

PATIENT 4

The patient was a 61 year old woman who was admitted to hospital in March 1975, because of deep thrombophlebitis in the right leg. The patient had fever raised ESR, and high WBC count (FIG. 6) with 14% leukaemic blasts in the blood smear. Acute myeloblastic leukaemia was diagnosed.

Four days later, the patient's white blood cell count had increased further (FIG. 6) with 80% abnormal blasts in the blood smear. A bone marrow aspirate was hypercellular and showed active, pathological myelopoiesis (over 90% of the cells were leukaemic blasts); other cell lineages appeared normal. The spleen, liver and lymph nodes were not enlarged. The patient had mild diabetes, controlled by diet, and the thrombophlebitis subsided after warfarin therapy.

Treatment

Full details of the chalone treatment given in this case appear in Table 14.

Chalone treatment was started with two daily injections of 10 mg (ca. 0.17 mg/kg; 2nd batch) increased to 20 mg after 3 days. After 13 day's treatment the patient was switched to injections of Batch 1 but, owing to its pyrogenicity, the dose had to be reduced (10 mg×2). Even so, the reactions were strong and accompanied by vomiting, and it soon became clear that the chalone dose was inadequate. Further regression of the leukaemia, or even maintenance of the improvement, was not possible with this dosage, and the treatment was discontinued.

TABLE 14

Treatment of Patient 4 with Chalone (Batches 1 and 2)

| | Chalone Dosage | |
|---|---|---|
| Day | Batch 2 | Batch 1 |
| 0 to 2 | 10mg × 2 | |
| 3 | 10mg and 20mg | |
| 4 to 6 | 20mg × 2 | |
| 7 | 20mg | |
| 8,9 | 20mg × 2 | |
| 10 | 20mg | |
| 11,12 | 20mg × 2 | |
| 13 to 17 | | 10mg × 2 |
| 18,19 | | No treatment |

TABLE 14-continued

| Treatment of Patient 4 with Chalone (Batches 1 and 2) | | |
|---|---|---|
| | Chalone Dosage | |
| Day | Batch 2 | Batch 1 |
| 20 | | 10mg |

Observations of Treatment

Figure 6:
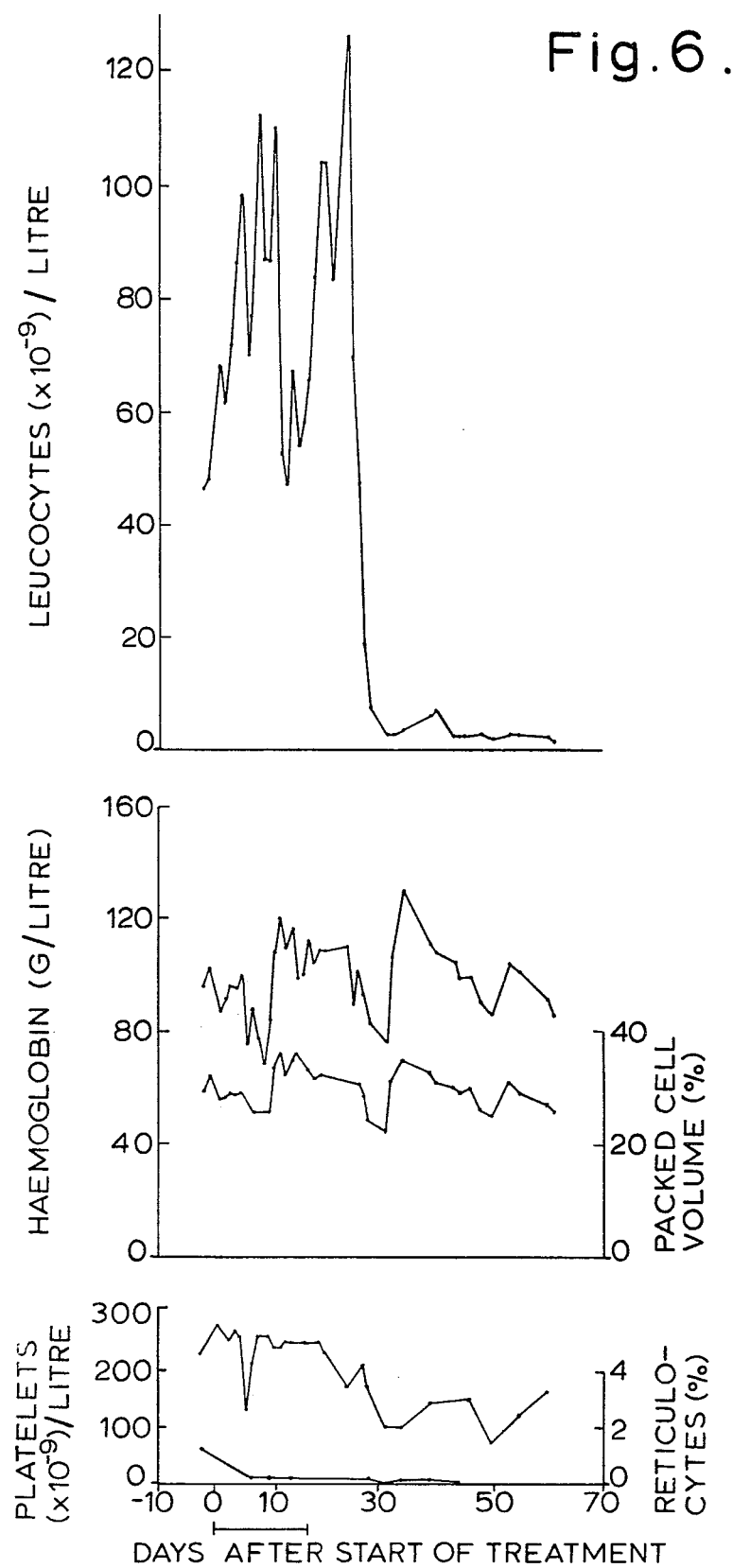

Haematological and biochemical data are shown in FIG. 6 and Table 15. The white blood cell count continued to rise for about a week after the onset of treatment; however, after 10 days the cell count decreased and the pre-treatment level was reached on day 13. Following the change in the chalone preparation on day 13, and the consequent reduction in chalone dosage, there was another rise in WBC count (FIG. 6 and Table 15).

On day 24 chemotherapy (thioguanine, daunorubicin, cytarabine, and prednisone) was started after a continued rise in WBC count.

TABLE 15

| DAY NUMBER | −2 | −1 | 0 | 1 | 2 | 3 | 4 | 5 | 6 | 7 | 8 | 9 | 10 |
|---|---|---|---|---|---|---|---|---|---|---|---|---|---|
| Leucocytes (Total) $\times 10^{-8}$ (cells/liter) | 46.2 | 48.1 | | 68.0 | 61.4 | 72.0 | 86.0 | 98.0 | 70.0 | 77.0 | 112.0 | 87 | 86.5 |
| Lymphocytes $\times 10^{-8}$ (cells/liter) | 1.6 | 4.8 | | | | 20.5 | | 44.1 | | 3.9 | | | 4.3 |
| Granulocytes $\times 10^{-8}$ (cells/liter) | 7.2 | 6.0 | | | | 12.2 | | 13.7 | | 25.4 | | | 16.0 |
| Promyelocytes (%) | 0 | 0 | | | | 0 | | 1.5 | | 1.5 | | | 2 |
| Myelocytes (%) | 4.5 | 0 | | | | 1.5 | | 2 | | 1.5 | | | 0 |
| Metamyelocytes (%) | 0.5 | 1.5 | | | | 1.0 | | 1.5 | | 14 | | | 1.0 |
| Band Cells (%) | 1 | 1 | | | | 6 | | 1 | | 3.5 | | | 4.5 |
| Polymorph Neutrophils (%) | 8.5 | 8.5 | | | | 7.5 | | 9.5 | | 13.5 | | | 13 |
| Total Neutrophils (%) | 14.5 | 12 | | | | 16 | | 14 | | 32.5 | | | 18.5 |
| Eosinophils (%) | 0.5 | 0 | | | | 0 | | 0 | | 0 | | | 0 |
| Basophils (%) | 0.5 | 0.5 | | | | 1 | | 0 | | 0.5 | | | 0 |
| Monocytes (%) | 0.5 | 0 | | | | 0 | | 0 | | 0.5 | | | 1 |
| Leukaemic Blasts (%) | 80.5 | 77.5 | | | | 54.5 | | 39.5 | | 60 | | | 70.5 |
| Lymphocytes (%) | 3.5 | 10 | | | | 28.5 | | 45 | | 5 | | | 8 |
| Erythrocytes $\times 10^{-12}$ (cells/liter) | 3.30 | 3.56 | | 3.11 | | 3.17 | 3.16 | 3.19 | | 2.79 | | | 2.79 |
| Reticulocytes (%) | 1.2 | | | | | | | | | 0.2 | | | 0.2 |
| Haemoglobin (g/liter) | 96 | 102 | | 87 | 91 | 96 | 95 | 100 | 75 | 87 | 77 | 68 | 84 |
| Haematocrit (%) | 29.3 | 32.0 | | 27.8 | | 28.6 | 28.4 | 28.8 | | 25.3 | | | 25.7 |
| E.S.R. (mm/hr) | | 35 | | | | | | | 90 | | | | |
| Platelets $\times 10^{-10}$ (cells/liter) | 230 | | | 280 | | 250 | 270 | 260 | 130 | 210 | 260 | | 260 |
| ASAT (SGOT) (units/liter) | | 36 | | | | | | 47 | | | | | |
| LDH (units/liter) | | 1735 | | | | | | 1635 | | | | | |
| Alkaline phosphatase (units/liter) | | 325 | | | | | | 370 | | | | | |
| Uric Acid (μmol/liter) | | 246 | | | | | | | | | | | |
| Creatinine (μmol/liter) | | 71 | | | | | | 95 | | | | | |
| Peroxidase +ve cells (%) | 15.5 | | | | | | | | | | | | |
| Alkaline phosphatase +ve cells (%) | 1.5 | | | | | | | | | | | | |

| DAY NUMBER | 11 | 12 | 13 | 14 | 15 | 16 | 17 | 18 | 19 | 20 | 21 | 24 | 25 |
|---|---|---|---|---|---|---|---|---|---|---|---|---|---|
| Leucocytes (Total) $\times 10^{-8}$ (cells/liter) | 110.0 | 52.8 | 47.0 | 67.2 | 53.4 | 58.0 | 66.0 | 84.0 | 104.0 | 104.0 | 83.0 | 126.0 | 69.9 |
| Lymphocytes $\times 10^{-8}$ (cells/liter) | | | | 27.6 | | | | | | 64.5 | | 63.0 | |
| Granulocytes $\times 10^{-8}$ (cells/liter) | | | | 11.8 | | | | | | 17.2 | | 22.7 | |
| Promyelocytes (%) | | | | 0 | | | | | | 0 | | 0 | |
| Myelocytes (%) | | | | 1 | | | | | | 2 | | 0 | |
| Metamyelocytes (%) | | | | 0.5 | | | | | | 1.5 | | 2 | |
| Band Cells (%) | | | | 2.5 | | | | | | 4 | | 5 | |
| Polymorph Neutrophils (%) | | | | 13.5 | | | | | | 9 | | 6 | |
| Total Neutrophils (%) | | | | 17.5 | | | | | | 16.5 | | 13 | |

TABLE 15-continued

| | | | | | | | | | | | |
|---|---|---|---|---|---|---|---|---|---|---|---|
| Eosinophils (%) | | | 0 | | | | | 0 | | 0 | |
| Basophils (%) | | | 0 | | | | | 0 | | 5 | |
| Monocytes (%) | | | 1 | | | | | 0 | | 0 | |
| Leukaemic Blasts (%) | | | 40.5 | | | | | 21.5 | | 35 | |
| Lymphocytes (%) | | | 41.0 | | | | | 62 | | 50 | |
| Erythrocytes $\times 10^{-12}$ (cells/liter) | 3.75 | 3.69 | 3.88 | | 3.59 | 3.43 | 3.49 | | | | |
| Reticulocytes (%) | | | 0.2 | | | | | | | | |
| Haemoglobin (g/liter) | 108 | 120 | 109 | 116 | 98 | 100 | 112 | 104 | 109 | 109 | 110 | 89 |
| Haematocrit (%) | 33.3 | 36.0 | 32.6 | 34.8 | 36.0 | | 33.0 | 31.2 | 32.0 | | | |
| E.S.R. (mm/hr) | 64 | | | | | | | | | | | |
| Platelets $\times 10^{-10}$ (cells/liter) | 240 | 240 | 250 | 250 | | | 250 | | 250 | 230 | 170 | |
| ASAT (SGOT) (units/liter) | | | | | | | 51 | | | | | |
| LDH (units/liter) | | | | | | | 1510 | | | | | |
| Alkaline phosphatase (units/liter) | | | | | | | 660 | | | | | |
| Uric Acid ($\mu$mol/liter) | | | | | | | | | | | | |
| Creatinine ($\mu$mol/liter) | | | | | | | 103 | | | | | |
| Peroxidase +ve cells (%) | | | | | | | | | | | | |
| Alkaline phosphatase +ve cells (%) | | | | | | | | | | | | |

| DAY NUMBER | 26 | 27 | 28 | 31 | 32 | 34 | 39 | 40 | 43 | 44 | 46 | 48 |
|---|---|---|---|---|---|---|---|---|---|---|---|---|
| Leucocytes (Total) $\times 10^{-8}$ (cells/liter) | 47.2 | 18.8 | 7.3 | 2.6 | 2.8 | 3.5 | 6.0 | 7.0 | 2.7 | 2.4 | 2.5 | 2.7 |
| Lymphocytes $\times 10^{-8}$ (cells/liter) | | 8.4 | 2.9 | 1.8 | | 2.3 | 5.0 | | 2.0 | | | |
| Granulocytes $\times 10^{-8}$ (cells/liter) | | 6.3 | 3.8 | 0.8 | | 1.1 | 0.2 | | 0.7 | | | |
| Promyelocytes (%) | | 0 | 0 | 0 | | 0 | 0 | | 0 | | | |
| Myelocytes (%) | | 1 | 0 | 0 | | 0 | 0 | | 0 | | | |
| Metamyelocytes (%) | | 0.5 | 0 | 0 | | 0 | 0 | | 0 | | | |
| Band Cells (%) | | 3.5 | 3.5 | 1 | | 1 | 0 | | 1 | | | |
| Polymorph Neutrophils (%) | | 28 | 49 | 31 | | 30 | 3 | | 24 | | | |
| Total Neutrophils (%) | | 33 | 52.5 | 32 | | 31 | 3 | | 25 | | | |
| Eosinophils (%) | | 0.5 | 0 | 0 | | 0 | 0 | | 0 | | | |
| Basophils (%) | | 0 | 0 | 0 | | 0 | 0 | | 0 | | | |
| Monocytes (%) | | 1 | 2.5 | 0 | | 2 | 3 | | 0 | | | |
| Leukaemic Blasts (%) | | 21 | 5 | 0 | | 0 | 10 | | 2 | | | |
| Lymphocytes (%) | | 44.5 | 40 | 68 | | 67 | 84 | | 73 | | | |
| Erythrocytes $\times 10^{-12}$ (cells/liter) | 3.43 | 3.23 | 2.82 | 2.57 | 3.61 | 4.21 | 3.77 | 3.66 | 3.58 | 3.32 | 3.31 | 3.14 |
| Reticulocytes (%) | | | 0.2 | 0.0 | | 0.1 | 0.1 | | 0.0 | | | |
| Haemoglobin (g/liter) | 101 | 93 | 83 | 76 | 106 | 130 | 111 | 108 | 104 | 99 | 99 | 90 |
| Haematocrit (%) | 30.6 | 28.3 | 24.0 | 22.0 | 31.0 | 35.0 | 32.4 | 30.3 | 30.0 | 29.0 | 30.0 | 26.0 |
| E.S.R. (mm/hr) | | | | | | | | | | | | |
| Platelets $\times 10^{-10}$ (cells/liter) | | 210 | 170 | 100 | | 100 | 140 | | | | 150 | |
| ASAT (SGOT) (units/liter) | | | | | | | | | | | | |
| LDH (units/liter) | | | | | | | | | | | | |
| Alkaline phosphatase (units/liter) | | | | | | | | | | | | |
| Uric Acid ($\mu$mol/liter) | | | | | | | | | | | | |
| Creatinine ($\mu$mol/liter) | | | | | | | | | | | | |
| Peroxidase +ve cells (%) | | | | | | | | | | | | |
| Alkaline phosphatase +ve cells (%) | | | | | | | | | | | | |

TABLE 15-continued

| DAY NUMBER | 50 | 53 | 55 | 60 | 61 |
|---|---|---|---|---|---|
| Leucocytes (Total) $\times 10^{-8}$ (cells/liter) | 2.0 | 2.4 | 2.3 | 2.0 | 1.0 |
| Lymphocytes $\times 10^{-8}$ (cells/liter) | | | | 1.2 | |
| Granulocytes $\times 10^{-8}$ (cells/liter) | | | | 0.7 | |
| Promyelocytes (%) | | | | 0 | |
| Myelocytes (%) | | | | 0 | |
| Metamyelocytes (%) | | | | 0 | |
| Band Cells (%) | | | | 2 | |
| Polymorph Neutrophils (%) | | | | 31 | |
| Total Neutrophils (%) | | | | 33 | |
| Eosinophils (%) | | | | 0 | |
| Basophils (%) | | | | 1 | |
| Monocytes (%) | | | | 0 | |
| Leukaemic Blasts (%) | | | | 8 | |
| Lymphocytes (%) | | | | 58 | |
| Erythrocytes $\times 10^{-12}$ (cells/liter) | 3.00 | 3.59 | 3.49 | 3.13 | 3.01 |
| Reticulocytes (%) | 0.0 | | | | |
| Haemoglobin (g/liter) | 86 | 104 | 101 | 91 | 85 |
| Haematocrit (%) | 25.0 | 30.4 | 28.5 | 26.4 | 25.6 |
| E.S.R. (mm/hr) | | | | | |
| Platelets $\times 10^{-10}$ (cells/liter) | 70 | | 120 | 160 | |
| ASAT (SGOT) (units/liter) | | | | | |
| LDH (units/liter) | | | | | |
| Alkaline phosphatase (units/liter) | | | | | |
| Uric Acid ($\mu$mol/liter) | | | | | |
| Creatinine ($\mu$mol/liter) | | | | | |
| Peroxidase +ve cells (%) | | | | | |
| Alkaline phosphatase +ve cells (%) | | | | | |

This drug therapy was followed by rapid fall in leucocyte count (FIG. 6 and Table 15), but complete remission was not achieved.

During the first half of the chalone treatment the patent's anaemia progressed rapidly (about 3 g/l per day). However, after red cell transfusions Hb remained essentially constant for about 2 weeks (FIG. 6 and Table 15). After the onset of drug therapy, haeomoglobin decreased again at a rapid rate (almost 5 g/l per day) and the effect of subsequent transfusions was then typically short-lasting. The patient had normal and essentially constant platelet counts during the periods of chalone treatment, but the situation deteriorated with the onset of drug therapy (see FIG. 6 and Table 15).

The data for this case show that initially there was regression of the disease but that this effect was lost when, as a direct result of the patient's inability to tolerate the pyrogenic nature of batch 1, the dose had to be halved. But for this the disease would probably have followed the pattern of the other acute cases, since on day 3 the patient's immunological capacity appeared adequae (immunoglobulin levels of 15.0, 3.3 and 2.0 g/liter of $I_gG$, $I_gA$ and $I_gM$ respectively were recorded). Furthermore, on day 24, at the commencement of standard drug therapy the patient's lymphocytes showed a reasonably good response to stimulation by phytohaemagglutinin.

Patient 5

This patient, the first of the three cases resistant to conventional chemotherapy, was a 61 year old woman with chronic granulocytic leukaemia, who had been treated since 1970 with busulphan and prednisone. In March 1975, a blastic crisis developed and the patient's white blood cell count rose to $160 \times 10^9$/l. Large doses of mercaptopurine decreased the cell count in 3 weks to $1.6 \times 10^9$/l. but after another 3 weeks the WBC count was again high ($101 \times 10^9$/l). A small dose of mercaptopurine was administered for three days before the patient was given chalone treatment.

On admission, the patient's general condition was poor with overt diabetes (requiring insulin therapy), presumably the result of protracted administration of prednisone. The spleen was enormous, extending below the umbilicus; the liver was moderately enlarged. The WBC count was high (see FIG. 7) with 60% leukaemic blasts in the blood smear; she was anaemic and her platelet count was subnormal.

Treatment

Full details of the chalone treatment and supportive treatment for patient 5 are given in Table 16.

Chalone treatment was started with two daily injections, each of 10 mg. (ca 0.17 mg/kg; 1st batch). After two days the preparation was changed (2nd batch) and on day 7 the dose was doubled. On day 3, after rupture of the spleen (see later), whilst still in shock (BP. 60/40 mmHg), the patient received chalone, which had no adverse effects. Chalone treatment was discontinued on day 9 because the patient's clinical status appeared hopeless (see later).

TABLE 16

Treatment of Patient 5 with Chalone (Batches 1 and 2)

| DAY | CHALONE DOSAGE | SUPPORTIVE TREATMENT |
|---|---|---|
| 0 | 10 mg × 2 (batch 1) | |
| 1 | 20 mg (batch 1) + 10 mg (batch 2) | |
| 2 to 5 | 10 mg × 2 (batch 2) | 6 units blood transfusion on day 3. |
| 6 | 10 mg & 20 mg (batch 2) | |
| 7 to 8 | 20 mg × 2 (batch 2) | |
| 9 | 20 mg × 2 (batch 2) | 2 units transfusion |

Observations on Treatment

Figure 7:
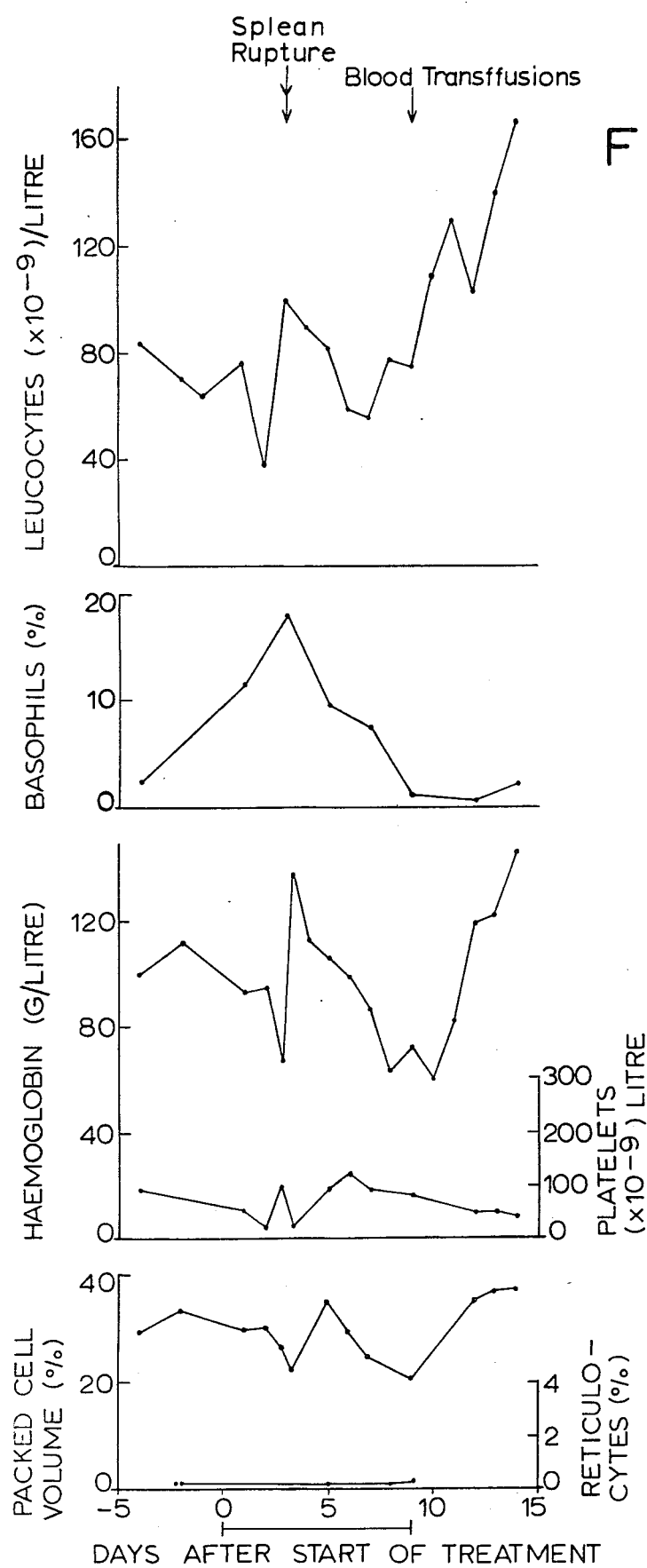

Haematological and biochemical data are given in Tables 17 and FIG. 7.

On day 3, about 12 hours after the last chalone dose, the patient's spleen ruptured spontaneously and she also began to bleed into the intestine. The rupture was detected immediately and shock was adequately counteracted by transfusion, but intra-abdominal and intestinal bleeding continued despite platelet transfusion.

The effect of chalone injections on WBC count in this case was overshadowed by the changes resulting from splenic rupture (Table 17 and FIG. 7). The only findings which suggest some effect on the leukemia were a change in blood basophil count (Table 17 and FIG. 7; note that basophilia is commonly considered a bad prognostic sign in chronic granulocytic leukaemia), and a temporary increase in LDH and alkaline phosphatase values, followed by a decrease to below the pre-treatment level (cf. other cases).

The patient died on day 14. Autopsy confirmed the clinical diagnoses, but revealed no signs of chalone-induced organ damage.

No conclusive statement can be made in this case regarding the effect of the chalone treatment on the leukaemic condition. However, the fact that the treatment was continued for several days after the splenic accident without aggravating the condition is an indication of its benign nature.

Patent 6

The patient was a 53 year old woman, in whom acute myeloblastic leukaemia was diagnosed in November 1974.

TABLE 17

(On day 3, two values for a single parameter represent measurements taken before/after spleen rupture).

| DAY NUMBER | −4 | −2 | −1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| Leucocytes (Total) × $10^{-8}$ (cells/liter) | 83.0 | 70.0 | 63.3 | 76.0 | 38.5 | 100/110 | | 90.0 | 82.0 | 19.0 | 6.0 | 8.0 | 75.0 | 108.0 | 130.0 | 102.6 | 140.0 | 167.0 |
| Lymphocytes × $10^{-8}$ (cells/liter) | 2.1 | | | 4.6 | | 16.5 | | | 17.2 | | 9.5 | | 0.8 | | | 2.1 | | 25.1 |
| Granulocytes × $10^{-8}$ (cells/liter) | 27.0 | | | 19.4 | | 25.0 | | | 21.7 | | 22.7 | | 22.9 | | | 29.8 | | 76.8 |
| Promyelocytes (%) | 4.5 | | | 26.5 | | 2.5 | | | 2.5 | | 4.5 | | 20.5 | | | 23.5 | | 13 |
| Myelocytes (%) | 5 | | | 1.5 | | 3.5 | | | 4.5 | | 9 | | 8 | | | 10.5 | | 21 |
| Metamyelocytes (%) | 5 | | | 1.5 | | 3.5 | | | 4.5 | | 9 | | 2 | | | 4.5 | | 5 |
| Band cells (%) | 1.5 | | | 3.5 | | 1.5 | | | 2 | | 3 | | 6 | | | 3.5 | | 8 |
| Polymorph Neutrophils (%) | 3.5 | | | 5 | | 1 | | | 3.5 | | 10.5 | | 13.5 | | | 10 | | 8 |
| Total Neutrophils (%) | 29 | | | 14 | | 14.5 | | | 16.5 | | 31.5 | | 29.5 | | | 28.5 | | 42 |
| Eosinophils | | | | | | | | | | | | | | | | | | |

TABLE 17-continued

| | | | | | | | | | | | | | | | | | |
|---|---|---|---|---|---|---|---|---|---|---|---|---|---|---|---|---|---|
| (%) Basophils | 1 | | 0 | | 1.5 | | 0.5 | | 1.5 | | 0 | | 0 | | | 2 | |
| (%) Monocytes | 2.5 | | 11.5 | | 18 | | 9.5 | | 7.5 | | 1 | | 0.5 | | | 2 | |
| (%) Leukaemic Blasts | 0 | | 0 | | 0 | | 1 | | 0.5 | | 0 | | 1 | | | 0 | |
| (%) Lymphocytes | 60.5 | | 42 | | 47 | | 49 | | 37.5 | | 48 | | 44.5 | | | 26 | |
| (%) Erythrocytes × 10⁻¹² (cells/liter) | 2.5 | | 6 | | 16.5 | | 21 | | 17 | | 1 | | 2 | | | 15 | |
| | 3.20 | 3.65 | 3.27 | 3.21 | 2.82/2.31 | | | | 3.25 | 2.69 | 2.18 | | 3.66 | | | 3.76 | |
| Reticulocytes (%) | | 0.1 | | | | | | | 0.1 | | 0.1 | | 0.2 | | | | |
| Haemoglobin (g/liter) | 100 | 112 | 93 | 95 | 83/67 | 138* | 113 | | 106 | 99 | 87 | 63 | 72 | 60 | 82 | 119 | 122 | 146 |
| Haematocrit (%) | 29.4 | 33.2 | 29.9 | 30.1 | 26.5/22.1 | | | | 35.0 | 29.3 | 24.7 | | 20.4 | | | 35.3 | 37.0 | 37.3 |
| E.S.R. (mm/hr) | 65 | | | | | | | | 55 | | 80 | | 80 | | | | | |
| Platelets × 10⁻¹⁰ (cells/liter) | 90 | | 50 | 20 | | 100/20 | | | 90 | 120 | 90 | | 80 | | | 50 | 50 | 40 |
| ASAT (SGOT) (units/liter) | 23 | | | | | | | | 21 | | 16 | | | | | | | |
| LDH (units/liter) | 3495 | | | | | | | | 6725 | | 3285 | | | | | | | |
| Alkaline phosphatase (units/liter) | 2165 | | | | | | | | 2650 | | 1560 | | | | | | | |
| Uric Acid (μmol/liter) | 413 | | | | | | | | 586 | | | | | | | | | |
| Creatinine (μmol/liter) | 97 | | | | | | | | 166 | 210 | 250 | | 270 | | | | | |
| Peroxidase +ve cells (%) | | 31.0 | | | | | | | | | | | | | | | | |
| Alkaline phosphatase (%) +ve cells | | 5.0 | | | | | | | | | | | | | | | | |

*After transfusion

In January and February 1975, the patient received 4 inductions at 10-day intervals with daunorubicin, cytarabine and prednisone; methotrexate and mercaptopurine were given as maintenane therapy. Complete remission of leukaemia was not achieved.

In April 1975, the patient was re-admitted to hospital in poor condition. She had fever (39° C.), high ESR, anaemia, thrombocytophenia, and raised white blood cell count (FIG. 8 and Table 21); about 80% of the blood cells were leukaemic blasts. Examinations showed that the patient had pleuritis, pericarditis, and maxillary sinuitis; she also suffered from cardiac damage of an unexplained type (probably not caused by daunorubicin since the total dose of this drug was below that accepted by the World Health organisation as being liable to cause cardiac damage. In the evening of the second day of chalone treatment (about 12 hr. after the last dose), the patient's already normalised temperature rose suddenly and cardiac arryhthemia was observed (both nodal and non-nodal rhythms were seen in electrocardiogram). The next day atrail flimmer developed which resulted in regular ventricular rhythm without overt clinical symptoms.

Treatment

Details of the chalone treatment and supportive treatment given are set out in Table 18.

Besides chalone injections and red cell transfusions, the patient received antibiotics (Globacillin (azidocillin) then chloramphenicol), digitalis and diuretics. Following the decision to apply chalone treatment, cytostatic drugs were withdrawn on day −4. Chalone treatment was started with one daily injection of 20 mg (ca. 0.36 mg/kg; 1st batch); after two days the dose was increased to 20 mg×2 (2nd and 3rd batches). The 1st batch caused a strong pyrogenic reaction, accompanied by vomiting and moderate respiratory distress, but the 2nd and 3rd batches were without side-effects. Following the remarkable improvement in her general condition, the patient elected to leave hospital and the treatment was therefore discontinued after day 19.

TABLE 18

| DAY | CHALONE DOSAGE | SUPPORTIVE TREATMENT |
|---|---|---|
| −2 to −1 | — | Blood transfusion (2 units) |
| | | Globacillin 150mg × 2 |
| | | Digoxin 0.25 × 1 |
| 0 to 1 | 20mg × 1 (batch 1) | Globacillin 150mg × 2 |
| 2 | 10mg × 1 (batch 2) | Globacillin 150mg × 2 |
| | | Digoxin 0.25 × 1 |
| 3 | 10mg × 2 (batch 2) | Globacillin 150mg × 2 |
| | | Digoxin 0.25 × 3 |
| 4 | 10mg × 2 (batch 2) | Globacillin 150mg × 2 |
| 5 | 20mg × 2 (batch 2) | Globacillin 150mg × 2 |
| 6 to 13 | 20mg × 2 (batch 2) | Globacillin 150mg × 2 |
| 14 | 20mg × 3 (batch 2) | Chloramphenicol 500mg × 3 |
| 15 to 19 | 20mg × 2 (batch 3) | Chloramphenicol 500mg × 3 |

Observations on Treatment

Figure 8:
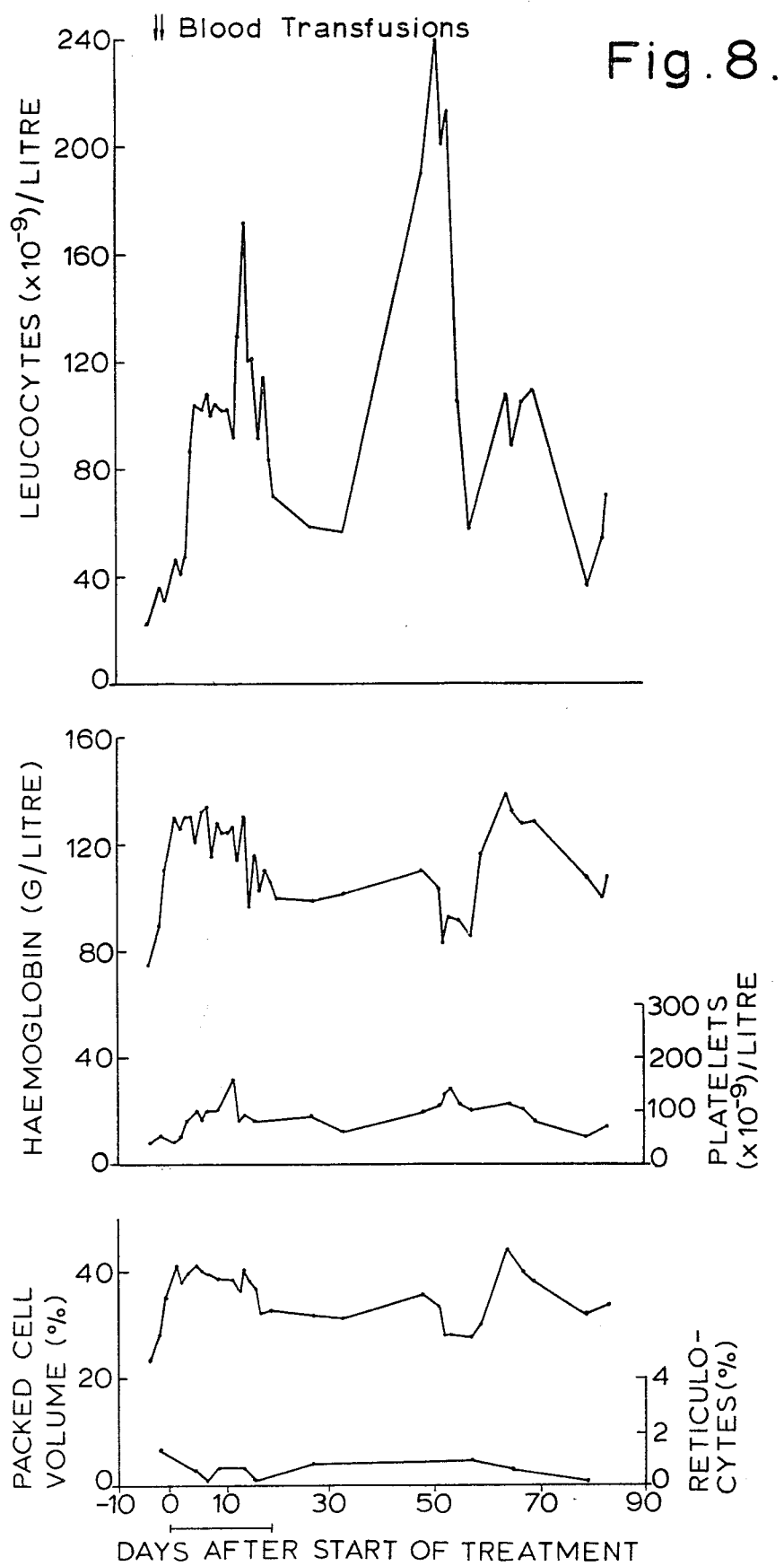

Biochemical and haematological data are given in Tables 19 and 20 and in FIG. 8.

After withdrawal of the drugs, there was a rise in the white blood cell count, and the effect of the chalone treatment was apparent only after 2 weeks when the WBC count began to decrease (Table 19 and FIG. 8). However an inhibition of leukaemic proliferation was suggested before this by bone marrow samples which showed that myelopoiesis had become morphologically more "chronic" than at the onset of the treatment.

It is recognised that in acute myeloid leukaemia there is a maturation arrest at an early stage in the sequence of development of the granulocytic series, e.g., at the promyelocyte or myelocyte level. In the chronic form of the disease this effect is less marked and a much wider spectrum of cell maturity within the granulocyte series is observed.

After the onset of chalone treatment the haemoglobin value decreased slowly for 3 weeks (ca. 1.5 g/l per day), but during the next month actually increased (Table 19 and FIG. 8). These reactions were in sharp contrast to the changes seen after resumption of drug therapy (Table 19 and FIG. 8). As in other patients, an indirect beneficial effect of chalone treatment was also reflected in platelet counts (see Table 19 and FIG. 8). An increase occurred which, even if less marked than in case 3 (FIG. 5), doubled the subnormal platelet count, this level being maintained for more than 1½ months.

There was a pronounced improvement in the patient's general condition during the chalone treatment, apparent from the subsidence of both the pleuritis and the pericarditis (revealed by successive X-ray studies). Both these complications were probably caused by leukaemic infiltration rather than bacteria, as judged from their exceptionally benign clinical course.

Later, whilst on maintenance therapy, other signs of leukaemic infiltration were seen e.g., the development of modules in the tissue of the lower eyelids. These eventually disappeared when, as a result of inadequate haematological response, the dose of cytotoxic drugs was increased.

After the cessation of chalone injections the WBC count continued to decrease for 2 weeks (Table 19 and FIG. 8); after a further 2 weeks, however, the cell count again rose and at this time during therapy (cyclophosphamide, cytarabine, prednisone) was resumed.

During February to April 1975, whilst on maintenance therapy, the patient's clinical condition was very poor. Treatment with chalone produced a dramatic improvement in this condition and was more successful in causing a favourable change in the haematological picture than methotrexate and mercaptopurine.

The patient's conditon had improved to such a degree that for personal reasons she elected to leave hospital. This decision was taken with the concurrence of her physician and no form of maintenance therapy was prescribed. Her condition remained good as borne out by the satisfactory haematological results obtained during two subsequent checks at weekly intervals. The patient was allowed to return home for a further two weeks without examination or maintenance therapy. Unfortunately, the situation deteriorated and events suggest that if chalone treatment had continued a more favourable clinical state would have been achieved.

TABLE 19

| DAY NUMBER | −4 | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Leucocytes (Total) × $10^{-8}$ (cells/liter) | 22.4 | | 36.3 | | 30.9 | | | 46.1 | 41.6 | 47.8 | 86.2 | 104.0 | 102.0 | 108.0 | 100.0 | 104.0 102.0 102.0 | 91.8 |
| Lymphocytes × $10^{-8}$ (cells/liter) | 2.1 | | 1.8 | | 1.4 | | | 1.0 | | 6.2 | | 3.2 | | 5.2 | | | 4.6 |
| Granulocytes × $10^{-8}$ (cells/liter) | 1.7 | | 4.4 | | 7.6 | | | 7.6 | | 30.2 | | 36.7 | | 46.3 | | | 43.6 |
| Promyelocytes (%) | 0 | | 1 | | 0 | | | | | 0 | | 0 | | 4.5 | | | 0.5 |
| Myelocytes (%) | 1 | | 1 | | 0.5 | | | 1 | | 9.5 | | 7 | | 12.5 | | | 10.5 |
| Metamyelocytes (%) | 0 | | 0 | | 1 | | | 1.5 | | 9 | | 9 | | 8 | | | 9.5 |
| Band Cells (%) | 0 | | 2 | | 6 | | | 4.5 | | 6.5 | | 0 | | 8 | | | 12.5 |
| Polymorph Neutrophils (%) | 6.5 | | 9 | | 9 | | | 8.5 | | 4 | | 18 | | 16 | | | 15 |
| Total Neutrophils (%) | 7.5 | | 12 | | 16.5 | | | 15.5 | | 29 | | 34 | | 44.5 | | | 47.5 |
| Eosinophils (%) | 0 | | 0 | | 0 | | | 0.5 | | 0 | | 0 | | 0 | | | 0 |
| Basophils (%) | 0 | | 0 | | 0 | | | 0 | | 0 | | 0 | | 0 | | | 0 |
| Monocytes (%) | 0.5 | | 0 | | 0 | | | 0 | | 0 | | 0 | | 0 | | | 1 |
| Leukaemic Blasts (%) | 82.5 | | 82.0 | | 80.5 | | | 82 | | 65.0 | | 67.0 | | 46.0 | | | 46.0 |

TABLE 19-continued

| | | | | | | | | | | | | | | |
|---|---|---|---|---|---|---|---|---|---|---|---|---|---|---|
| Lymphocytes (%) | 9.5 | 5 | 3 | 2 | 6 | | 3 | 5 | | 5 | | | | |
| Erythrocytes $\times 10^{-12}$ (cells/liter) | 2.34 | 2.85 | 3.63 | 4.23 | 3.96 | 4.15 | | 4.05 | 4.0 | 3.91 | | | 3.83 | |
| Reticulocytes (%) | | 13 | | | | | | 0.5 | 0.1 | 0.6 | | | | |
| Haemoglobin (g/liter) | 75 | 89 | 110 | 130 | 125 | 130 | 130 | 120 | 132 | 134 | 115 | 128 | 124 | 124 | 125 |
| Haematocrit (%) | 23.0 | 27.9 | 34.9 | 40.7 | 37.9 | 39.6 | | 41.0 | 40.0 | 39.6 | | 38.4 | | | 38.3 |
| E.S.R. (mm/hr) | 99 | | | | 36 | | | | | 47 | | | | | 50 |
| Platelets $\times 10^{-10}$ (cells/liter) | 40 | 50 | | 40 | 50 | 80 | | 100 | 80 | 100 | | 100 | | | 160 |
| ASAT (SGOT) (units/liter) | | | | | | 12 | | | 16 | | | | | | |
| LDH (units/liter) | | | | | | 1025 | | | 970 | | | | | | |
| Alkaline phosphatase (units/liter) | | | | | | | | | 110 | | | | | | |
| Uric Acid (μmol/liter) | | | | | | | | | 413 | | | | | | |
| Creatinine (μmol/liter) | | | | | | | | | 93 | | | | | | |
| Peroxidase +ve cells (%) | | 77 | 12.0 | | | | | | | | | | | | |
| Alkaline phosphatase +ve cells (%) | | | 7.5 | | | | | | | | | | | | |

| DAY NUMBER | 13 | 14 | 15 | 16 | 17 | 18 | 19 | 20 | 27 | 33 | 48 | 49 |
|---|---|---|---|---|---|---|---|---|---|---|---|---|
| Leucocytes (Total) $\times 10^{-8}$ (cells/liter) | 130.0 | 172.0 | 120.0 | 120.3 | 91.0 | 114.0 | 83.0 | 69.0 | 58.2 | 56.0 | 190.0 | |
| Lymphocytes $\times 10^{-8}$ (cells/liter) | | 12.9 | | 31.9 | | | 6.6 | | 16.9 | | | |
| Granulocytes $\times 10^{-8}$ (cells/liter) | | 83.4 | | 54.7 | | | 24.1 | | 18.6 | | | |
| Promyelocytes (%) | | 0 | | 0 | | | 0 | | 0 | | | |
| Myelocytes (%) | | 3 | | 1 | | | 3.5 | | 5 | | | |
| Metamyelocytes (%) | | 7.5 | | 3 | | | 2.5 | | 3 | | | |
| Band Cells (%) | | 19.5 | | 14.5 | | | 5 | | 2 | | | |
| Polymorph Neutrophils (%) | | 18.5 | | 27 | | | 18 | | 22 | | | |
| Total Neutrophils (%) | | 48.5 | | 45.5 | | | 29 | | 32 | | | |
| Eosinophils (%) | | 0 | | 0 | | | 0 | | | | | |
| Basophils (%) | | 0 | | 0 | | | 0 | | 0 | | | |
| Monocytes (%) | | 1 | | 0 | | | 3 | | 4 | | | |
| Leukaemic Blasts (%) | | 47 | | 28 | | | 60 | | 35 | | | |
| Lymphocytes (%) | | 7.5 | | 26.5 | | | 8 | | 29 | | | |
| Erythrocytes $\times 10^{-12}$ (cells/liter) | 3.66 | 3.98 | | 3.10 | | | 3.23 | | 3.25 | 3.14 | 3.33 | |
| Reticulocytes (%) | | 0.6 | | 0.2 | | | | | 0.8 | | | |
| Haemoglobin (g/liter) | 114 | 131 | 96 | 116 | 102 | 110 | 106 | 100 | 99 | 101 | 110 | |
| Haematocrit (%) | 36.1 | 40.3 | 38.0 | 36.4 | 32.0 | | 32.8 | | 31.7 | 31.0 | 35.8 | |
| E.S.R. (mm/hr) | | | | | | | | | | | | |
| Platelets $\times 10^{-10}$ (cells/liter) | 80 | 90 | | 80 | | | | | 90 | 60 | 100 | |
| ASAT (SGOT) (units/liter) | | 15 | | | | | | | | | | |
| LDH (units/liter) | | 885 | | | | | | | | | | |
| Alkaline phosphatase (units/liter) | | 120 | | | | | | | | | | |
| Uric Acid (μmol/liter) | | 461 | | | | | | | | | | |
| Creatinine (μmol/liter) | | 75 | | | | | | | | | 100 | |
| Peroxidase +ve cells (%) | | | | | | | | | | | | |
| Alkaline phosphatase +ve cells (%) | | | | | | | | | | | | |

| DAY NUMBER | 51 | 52 | 53 | 55 | 57 | 58 | 59 | 64 | 65 | 67 | 69 | 79 | 82 | 83 |
|---|---|---|---|---|---|---|---|---|---|---|---|---|---|---|
| Leucocytes (Total) $\times 10^{-8}$ (cells/liter) | 40.0 | 00.0 | 14.0 | 05.0 | 57.2 | | | 08.0 | 88.0 | 05.0 | 10.0 | 35.9 | 54.0 | 70.0 |
| Lymphocytes $\times 10^{-8}$ (cells/liter) | | | | | 10.9 | | | | | | | 0.4 | | |
| Granulocytes $\times 10^{-8}$ (cells/liter) | | | | | 19.4 | | | | | | | 3.4 | | |
| Promyelocytes (%) | | | | | 0 | | | | | | | 0 | | |
| Myelocytes (%) | | | | | 1 | | | | | | | 0 | | |
| Metamyelocytes (%) | | | | | 2 | | | | | | | 0.5 | | |
| Bane Cells (%) | | | | | 3 | | | | | | | 1.5 | | |
| Polymorph Neutrophils (%) | | | | | 28 | | | | | | | 7.5 | | |
| Total Neutrophils (%) | | | | | 34 | | | | | | | 9.5 | | |
| Eosinophils (%) | | | | | 0 | | | | | | | 0 | | |
| Basophils (%) | | | | | 0 | | | | | | | 0 | | |
| Monocytes (%) | | | | | 4 | | | | | | | 1 | | |
| Leukaemic Blasts (%) | | | | | 43 | | | | | | | 88.5 | | |
| Lymphocytes (%) | | | | | 19 | | | | | | | 1 | | |
| Erythrocytes | | | | | | | | | | | | | | |

TABLE 19-continued

| × $10^{-12}$ (cells/liter) | 3.06 | | | | 2.76 | | 4.43 | | 3.99 | 3.97 | 3.41 | | 3.45 |
|---|---|---|---|---|---|---|---|---|---|---|---|---|---|
| Reticulocytes (%) | | | | | 0.9 | | | 0.6 | | | 0.1 | | |
| Haemoglobin (g/liter) | 103 | 82 | 93 | 91 | 85 | 116 | 139 | 132 | 128 | 129 | 108 | 100 | 108 |
| Haematocrit (%) | 33.3 | 27.9 | 28.0 | | 27.6 | 30.0 | 43.9 | | 40.0 | 38.1 | 32.0 | | 33.4 |
| E.S.R. (mm/hr) | 56 | 41 | | | 46 | | | 24 | | 32 | 84 | | |
| Platelets × $10^{-10}$ (cells/liter) | 110 | 130 | 140 | 110 | 100 | | 110 | | 100 | 80 | 50 | | 70 |
| ASAT (SGOT) (units/liter) | 17 | 21 | | | | | | 24 | | | | | |
| LDH (units/liter) | 850 | 810 | | | | | | 545 | | | | | |
| Alkaline phosphatase (units/liter) | | | | | | | | 160 | | | | | |
| Uric Acid (μmol/liter) | | | | | | 280 | | 482 | | | | | |
| Creatinine (μmol/liter) | | | | | | | | 73 | | | 90 | | |
| Peroxidase + ve cells (%) | | | | | | | | | | | | | |
| Alkaline phosphatase + ve cells (%) | | | | | | | | | | | | | |

TABLE 20

Serum Immunoglobulin Levels (g./liter) (Patient 6)

| Day No. | IgG | IgM | IgM |
|---|---|---|---|
| 14 | 18 | 2.4 | 2.5 |
| 27 | 15 | 1.7 | 1.7 |

Patient 7

The patient was a 44 year old man first seen in October 1974 when acute myeloblastic leukaemia was diagnosed. Three inductions (thioguanine, daunorubicin, cytarabine, and prednisone), followed by maintenance therapy with methotrexate and mercaptopurine, decreased the WBC count from $126 \times 10^9/l$ to $1 \times 10^9/l$. Drug therapy resulted in hypoplastic bone marrow with persistently low white blood cell count, episodes of severe thrombocytopenia (occasionally only $5 \times 10^9/l$), and recurrent rapid development of anaemia (ca. 2 g/l per day). Reduced drug dosage, frequent transfusions, and administration of anabolic steroids considerably improved the patient's clinical status.

In March 1975, the patient's white blood cell count rose slowly, but it was still less than $10 \times 10^9/l$ (10–20% abnormal blasts) on admission to hospital for chalone treatment. He had severe anaemia, but his platelet count was normal (Table 22 and FIG. 9); His general condition was fairly good without complicating diseases. It was considered that a further induction would be of doubtful clinical value and the patient was selected for chalone therapy. Cytostatic drugs were withdrawn on day −4 and anabolic steroids on day 0.

Treatment

Details of chalone dosage and supportive treatment given to patient 7 are set out in Table 21.

Chalone treatment commenced with two daily injections of 10 mg (ca. 0.14 mg/kg; 2nd batch), progressively increased to 2×40 mg (3rd batch) on day 14. At first aspirin was given to counteract possible pyrogenic reaction (1 to 1.5×2), but was later withdrawn without the appearance of side-effects until the maximum dose was reached, when a strong pyrogenic reaction was observed.

TABLE 21

Treatment of Patient 7 with Chalone (Batches 2 and 3)

| DAY | CHALONE DOSAGE | | SUPPORTIVE TREATMENT |
|---|---|---|---|
| 0 | 20mg × 1 | (batch 2) | |
| 1 | 20mg × 1 | | |
| | | (batch 2) | |
| | 10mg × 1 | | Aspirin (1g) with each injection |
| 2 | 10mg × 2 | (batch 2) | |
| 3 | 10mg × 1 | | |
| | | (batch 2) | |
| | 20mg × 1 | | |
| 4 to 7 | 20mg × 2 | (batch 2) | |
| 8 | 20mg × 1 | (batch 2) | |
| | 40mg × 1 | | No aspirin |
| 9 to 12 | 40mg × 2 | (batch 2) | |
| 13 | 40mg × 1 | (batch 2) | No aspirin |
| | 20mg × 1 | (batch 3) | Aspirin (1.5g) with each injection |
| 14 to 17 | 40mg × 2 | (batch 3) | Aspirin (1.5g) with each injection |

Observations on Treatment

Figure 9:
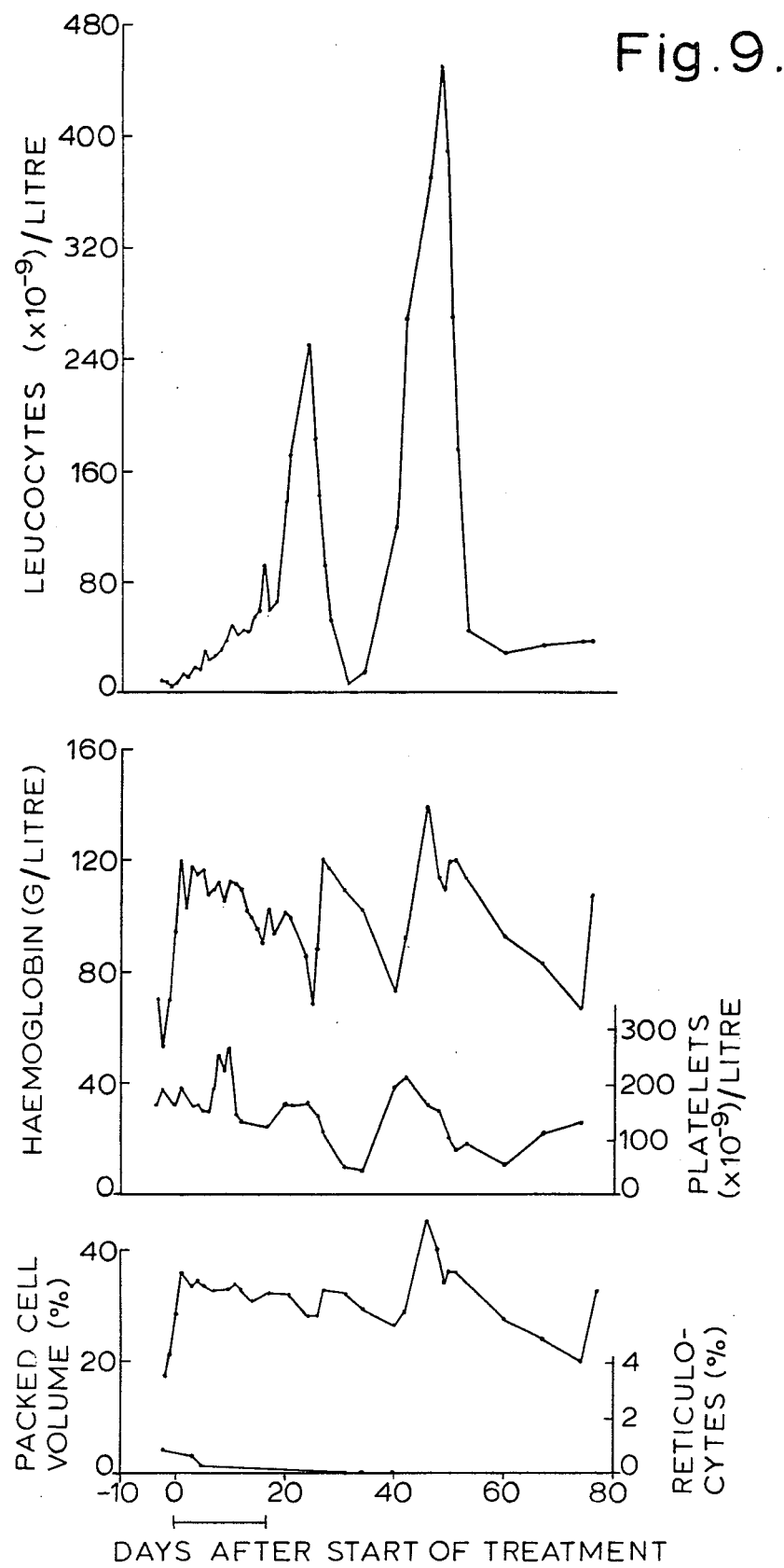

The biochemical and haematological data for patient 7 are set out in Table 22 and shown in FIG. 9.

As in case 6, withdrawal of cytostatic drugs was followed by a rise in the WBC count (up to 70% of the cells were now abnormal blasts), but in this patient the trend could not be reversed, or even stopped, by chalone treatment. However, there is no doubt that chalone injections retarded strongly the rate of WBC increase; this became clear when the cessation of chalone treatment was immediately followed by a 10-fold acceleration of the increase (Table 24 and FIG. 8). Strong inhibition of leukaemic proliferation by chalone is also apparent from the rate of white blood cell increase after the drug-induced fall in the cell count (Table 24 and FIG. 9); in 18 days the WBC count rose from $6 \times 10^9/l$ to an unusually high value of $450 \times 10^9/l$, whereas during the chalone treatment the rise in a similar period was from $6 \times 10^9/l$ to only $65 \times 10^9/l$.

It is clear from these comparisons that chalone injections must have profoundly inhibited leukaemic proliferation, perhaps by 80 to 90%. This may be more than that achieved in any other patient (with the possible exception of patient 1), but it nevertheless failed to induce regression of the leukaemia.

During the chalone treatment the patient's haemoglobin value decreased more slowly than during the periods of drug therapy (about 1 and 2 g/l per day, respectively; see also Table 22 and FIG. 9). The platelet count was unchanged during chalone injections (Table 22 and FIG. 9), but fell rapidly after the onset of drug therapy (with thioguanine, daunorubicin, cytarabine, prednisone, and later vincristine, cyclophosphamide, methotrexate, and mercaptopurine).

It may be noted that this patient received chalone as an out-patient for about 10 days, and during this period his general condition remained good or, according to his own account, was even improved; as a consequence, he returned to work.

If chalone treatment had been continued at the maximum tolerated dose and the rate of increase of leucocytes had been maintained at that seen during the first fifteen days of treatment, the ultimate high level of white cells would not have been reached until approximately day 150. Under treatment with cytotoxic drugs the patient died on day 117.

TABLE 22

| DAY NUMBER | −3 | −2 | −1 | 0 | 1 | 2 | 3 | 4 | 5 | 6 | 7 | 8 | 9 |
|---|---|---|---|---|---|---|---|---|---|---|---|---|---|
| Leucocytes (Total) × $10^{-8}$ (cells/liter) | 8.2 | 7.9 | 4.9 | 6.8 | 13.2 | 11.3 | 18.5 | 16.8 | 29.5 | 24.1 | 26.1 | 29.4 | 36.9 |
| Lymphocytes × $10^{-8}$ (cells/liter) | | 1.3 | | 3.5 | 5.9 | | 6.6 | | 9.1 | | 1.7 | | |
| Granulocytes × $10^{-8}$ (cell/liter) | | 2.8 | | 2.3 | 6.7 | | 5.5 | | 6.8 | | 4.6 | | |
| Promyelocytes (%) | | 1.5 | | 0 | 0 | | 0 | | | | 1.5 | | |
| Myelocytes (%) | | 1 | | 1 | 0 | | 0.5 | | 1 | | 2.5 | | |
| Metamyelocytes (%) | | 1 | | 1 | 1 | | 1.5 | | 1 | | 2 | | |
| Band Cells (%) | | 1 | | 0 | 1 | | 0 | | 0 | | 0.5 | | |
| Polymorph Neutrophilis (%) | | 32.5 | | 32 | 49 | | 27 | | 21 | | 12.5 | | |
| Total Neutrophilis (%) | | 35.5 | | 34 | 51 | | 29 | | 23 | | 17.5 | | |
| Eosinophils (%) | | 0 | | 0 | 0 | | 0 | | 0 | | 0 | | |
| Basophils (%) | | 0 | | 0 | 0 | | 0.5 | | 0 | | 0 | | |
| Monocytes (%) | | 0 | | 4 | 1 | | 4 | | 3 | | 1 | | |
| Leukaemic Blasts (%) | | 46.5 | | 10 | 3 | | 31 | | 43 | | 73.5 | | |
| Lymphocytes (%) | | 16.5 | | 52 | 45 | | 35.5 | | 31 | | 6.5 | | |
| Erythrocytes × $10^{-12}$ (cells/liter) | | 2.04 | | 3.31 | 4.09 | | 3.88 | 3.94 | 3.85 | | 3.71 | | |
| Reticulocytes (%) | | 0.8 | | | | | | 0.6 | 0.2 | | | | |
| Haemoglobin (g/liter) | 70 | 53 | 70 | 94 | 120 | 103 | 118 | 115 | 116 | 107 | 109 | 112 | 105 |
| Haematpcrit (%) | | 17.1 | 21.0 | 28.3 | 35.7 | | 33.5 | 34.7 | 33.7 | | 32.4 | | |
| E.S.R. (mm/hr) | | 20 | | | | | 20 | | | | | | |
| Platelets × $10^{-10}$ (cells/liter) | 160 | 190 | | 160 | 190 | | 160 | 160 | 150 | 150 | 190 | 250 | 220 |
| ASAT (SGOT) (units/liter) | 35 | | | 34 | | 34 | | | | | | | |
| LDH (units/liter) | | 675 | | | | | | | | | | | |
| Alkaline phosphatase (units/liter) | | 105 | | | 135 | | 135 | | | | | | |
| Uric Acid (μmol/liter) | | | | | 276 | | | | 243 | | | | |
| Creatimine (μmol/liter) | | 103 | | | 105 | | | | | | | | |
| Peroxidase +ve cells (%) | | | | | | | | | | | | | |
| Alkalime phophatase +ve cells (%) | | | | | | | | | | | | | |

| DAY NUMBER | 10 | 11 | 12 | 13 | 14 | 15 | 16 | 17 | 18 | 20 | 21 | 24 |
|---|---|---|---|---|---|---|---|---|---|---|---|---|
| Leucocytes (Total) × $10^{-8}$ (cell/liter) | 45.8 | 41.0 | 44.5 | 43.0 | 54.0 | 59.2 | 92.0 | 59.1 | 66.0 | 138.0 | 170.0 | 250.0 |
| Lymphocytes × $10^{-8}$ (cell/liter) | 2.1 | 14.1 | 12.0 | | 7.0 | | | 5.9 | | | 12.8 | 22.5 |
| Granulocytes × $10^{-8}$ (cell/liter) | 9.6 | 7.4 | 6.2 | | 7.6 | | | 18.9 | | | 33.2 | 43.8 |
| Promyelocytes (%) | 0 | 0 | 0 | | 0 | | | 0 | | | 0 | 0 |
| Myelocytes (%) | 2 | 0 | 0 | | 1.5 | | | 5 | | | 0.5 | 1.5 |
| Metamyelocytes (%) | 0.5 | 1.5 | 1 | | 1.5 | | | 1 | | | 2 | 0.5 |
| Band Cells (%) | 1.5 | 1 | 2 | | 2.5 | | | 0 | | | 4 | 2.5 |
| Polymorph Neutrophils (%) | 17 | 15.5 | 11 | | 8.5 | | | 26 | | | 13 | 13 |
| Total Neutrophils (%) | 21 | 18 | 14 | | 14 | | | 32 | | | 19.5 | 17.5 |
| Eosinophils (%) | 0 | 0 | 0 | | 0 | | | 0 | | | 0 | 0 |
| Basophils (%) | 0 | 0 | 0 | | 0 | | | 0 | | | 0 | 0 |
| Monocytes (%) | 0 | 3 | 0 | | 0 | | | 2 | | | 0 | 0 |
| Leukaemic Blasts (%) | 74.5 | 44.5 | 59 | | 73 | | | 61 | | | 73 | 73.5 |
| Lymphocytes (%) | 4.5 | 34.5 | 27 | | 13 | | | 10 | | | 7.5 | 9 |
| Erythrocytes × $10^{-12}$ (cells/liter) | 3.67 | 3.83 | 3.68 | | 3.33 | | | 3.32 | | | 3.18 | 3.31 |
| Reticulocytes (%) | | | | | | | | | | | | |
| Haemoglobin (g/liter) | 112 | 111 | 109 | 101 | 99 | 95 | 90 | 102 | 94 | 101 | 99 | 85 |
| Haematocrit (%) | 32.7 | 34.0 | 32.7 | | 30.3 | | | 32.0 | | | 31.3 | 28.0 |
| E.S.R. (mm/hr) | | | | | | | | | | | | 71 |
| Platelets × $10^{-10}$ (cells/liter) | 260 | 140 | 130 | | | | | 120 | | 160 | 160 | 160 |
| ASAT (SGOT) (units/liter) | | | | | | | | 62 | | | | |
| LDH (units/liter) | | | | | | | | 2095 | | | | |
| Alkaline phosphatase (units/liter) | | | | | | | | | | | | |
| Uric Acid (μmol/liter) | | | | | | | | | | | | |
| Creatinine (μmol/liter) | | | | | 112 | | | | | | | |
| Peroxidase +ve cells (%) | | | | | | | | | | | | |
| Alkaline phosphatase | | | | | | | | | | | | |

TABLE 22-continued

| +ve cells (%) | | | | | | | | | | | |
|---|---|---|---|---|---|---|---|---|---|---|---|
| DAY NUMBER | 25 | 26 | 27 | 28 | 31 | 34 | 40 | 42 | 46 | 48 | 49 |
| Leucocytes (Total) $\times 10^{-8}$ (cells/liter) | 183.0 | 142.0 | 93.0 | 52.1 | 6.4 | 15.8 | 118.0 | 270.0 | 370.0 | 450.0 | 390.0 |
| Lymphocytes $\times 10^{-8}$ (cells/liter) | | | 2.3 | | 2.6 | 1.1 | 5.9 | | | | |
| Granulocytes $\times 10^{-8}$ (cells/liter) | | | 1.9 | | 1.5 | 2.1 | 15.9 | | | | |
| Promyelocytes (%) | | | 0 | | 0 | 0 | 0 | | | | |
| Myelocytes (%) | | | 0.5 | | 0 | 0 | 0 | | | | |
| Metamyelocytes (%) | | | 0 | | 0 | 1 | 5 | | | | |
| Band Cells (%) | | | 2.5 | | 0 | 1 | 3.5 | | | | |
| Polymorph Neutrophils (%) | | | 17 | | 24 | 3 | 5 | | | | |
| Total Neutrophils (%) | | | 20 | | 24 | 5 | 13.5 | | | | |
| Eosinophils (%) | | | 0 | | 0 | 0 | 0 | | | | |
| Basophils (%) | | | 0 | | 0 | 0 | 0 | | | | |
| Monocytes (%) | | | 0 | | 0 | 0 | 0 | | | | |
| Leukaemic Blasts (%) | | | 77.5 | | 36 | 88 | 90 | | | | |
| Lymphocytes (%) | | | 2.5 | | 40 | 7 | 5 | | | | |
| Erythrocytes $\times 10^{-12}$ (cells/liter) | | 3.32 | 3.32 | | 3.64 | 3.30 | 2.74 | | 4.09 | | |
| Reticulocytes (%) | | | | | 0.0 | | | | | | |
| Haemoglobin (g/liter) | 68 | 89 | 120 | 117 | 109 | 102 | 72 | 92 | 139 | 113 | 109 |
| Haematocrit (%) | | 28.2 | 32.6 | | 32.0 | 29.0 | 26.6 | 29.0 | 45.3 | 40.0 | 34.0 |
| E.S.R. (mm/hr) | | | | | | | | | | | |
| Platelets $\times 10^{-10}$ (cells/liter) | | 140 | 110 | | 50 | 40 | 190 | 210 | 160 | 150 | |
| ASAT (SGOT) (units/liter) | | | | | | | | | | | |
| LDH (units/liter) | | | | | | | | | | | |
| Alkaline phosphatase (units/liter) | | | | | | | | | | | |
| Uric Acid (μmol/liter) | | | | | | | | | | | |
| Creatinine (μmol/liter) | | | | | | | | | | | |
| Peroxidase +ve cells (%) | | | | | | | | | | | |
| Alkaline phosphatase +ve cells (%) | | | | | | | | | | | |

| DAY NUMBER | 50 | 51 | 53 | 60 | 67 | 74 | 76 |
|---|---|---|---|---|---|---|---|
| Leucocytes (Total) $\times 10^{-8}$ (cells/liter) | 270.0 | 174.0 | 44.0 | 28.0 | 34.5 | 37.0 | 37.5 |
| Lymphocytes $\times 10^{-8}$ (cells/liter) | | | | | | 3.1 | |
| Granulocytes $\times 10^{-8}$ (cells/liter) | | | | | | 1.7 | |
| Promyelocytes (%) | | | | | | 0 | |
| Myelocytes (%) | | | | | | 0.5 | |
| ,etamyelocytes (%) | | | | | | 0 | |
| Band Cells (%) | | | | | | 0.5 | |
| Polymorph Neutrophils (%) | | | | | | 3.5 | |
| Total Neutrophils (%) | | | | | | 4.5 | |
| Eosinophils (%) | | | | | | 0 | |
| Basophils (%) | | | | | | 0 | |
| Monocytes (%) | | | | | | 0 | |
| Leukaemic Blasts (%) | | | | | | 87 | |
| Lymphocytes (%) | | | | | | 8.5 | |
| Erythrocytes $\times 10^{-12}$ (cells/liter) | | | | 3.20 | | 3.79 | |
| Reticulocytes (%) | | | | | | | |
| Haemoglobin (g/liter) | 119 | 120 | 113 | 92 | 83 | 67 | 107 |
| Haematocrit (%) | 36.0 | 36.0 | | 27.5 | 24.0 | 20.0 | 32.7 |
| E.S.R. (mm/hr) | | | | | | | |
| Platelets $\times 10^{-10}$ (cells/liter) | 100 | 80 | 90 | 50 | 110 | 130 | |
| ASAT (SGOT) (units/liter) | | | | | | | |
| LDH (units/liter) | | | | | | | |
| Alkaline phosphatase (units/liter) | | | | | | | |
| Uric Acid (μmol/liter) | | | | | | | |
| Creatinine (μmol/liter) | | | | | | | |
| Peroxidase +ve cells (%) | | | | | | | |
| Alkaline phosphatase (%) +ve cells | | | | | | | |

The preceding case histories demonstrate the biological effect of granulocytic chalone in humans with myeloid leukaemia.

In a population of cells, if cell production is suppressed strongly enough to reduce it to less than the rate of spontaneous cell loss, then the cell population will regress. Chalone would appear to be acting to suppress production of target cells, perhaps acting as an adjunct to, and at the same time, perhaps stimulating the normal defence mechanisms of the body.

The results obtained with the present clinical cases of treatment of myeloid leukaemia with granulocytic chalone, show that granulocytic chalone selectivity inhibited proliferation of leukaemic and normal granulocytic cells in man, without having a marked effect on other cell lineages. There was no inhibition of erythropoiesis and megakaryopoiesis (and in fact these activities were enhanced), no evidence of cell cytotoxicity but evidence that serum immunoglobulin values were increased. The conclusion that granulocytic chalone did not destroy leukaemic cells directly is supported by in vitro studies, in which chalone concentrations greater by 100-fold than any concentration to be expected in the bone marrow druing the therapy described were without toxic effect.

The rate of cell death in the leukaemic population nevertheless increased after the onset of chalone treatment. This is clearly evident from the increased levels of serum enzymes and urate values.

The degree of specificity of the granulocytic chalone is not only clear from the haematological data but from other evidence such as unaltered hair growth, normal healing of skin wounds, non-ulceration of mucous membranes and remarkable resistance to bacterial infection (all observed with patient 3).

Inhibition of leukaemic growth was observed in all cases and a regression was noted. Although full remission by the currently accepted criterion of less than 5% abnormal cells in the bone marrow was achieved in only one of the five acute cases, two of the patients were able to resume a normal life for several months without maintenance therapy of any kind. It is possible that at higher dose levels full remissions could have been obtained. In one of the two chronic cases improvement of the general clinical condition could not be expected due to the overriding symptoms of severe respiratory disease. In the other case the situation became irretrievable after rupture of the spleen.

The major advantage in chalone therapy is that its suppressive action is confined to the particular cell-type from which the leukaemic population arises. The pancytopaenia seen after treatment with conventional chemotherapy does not occur. Suppression of erythropoiesis and megakaryopoiesis, leading to anaemia and haemorrhage which are the usual causes of death in myeloid leukaemia, do not result from chalone therapy but these activities are, in fact, increased.

Another important advantage is that the patient's immune defence system is unimpaired, even enhanced, by chalone treatment. The remarkable resistance to infection at the low levels of circulating granulocytes following injections of the chalone preparations illustrates this aspect. It is possible that the normal humoral and cell-mediated immune mechanisms which appear to be enhanced by the chalone, are augmented by stimulation of additional systems, such as the complement system. The presence in the preparations of agents other than granulocytic chalone, which may act on the immune mechanism, is a possibility.

In addition to the use of chalone on its own, there is the possibility of its therapeutic use in combination with other forms of treatment, particularly immunotherapy.

Figure 10:
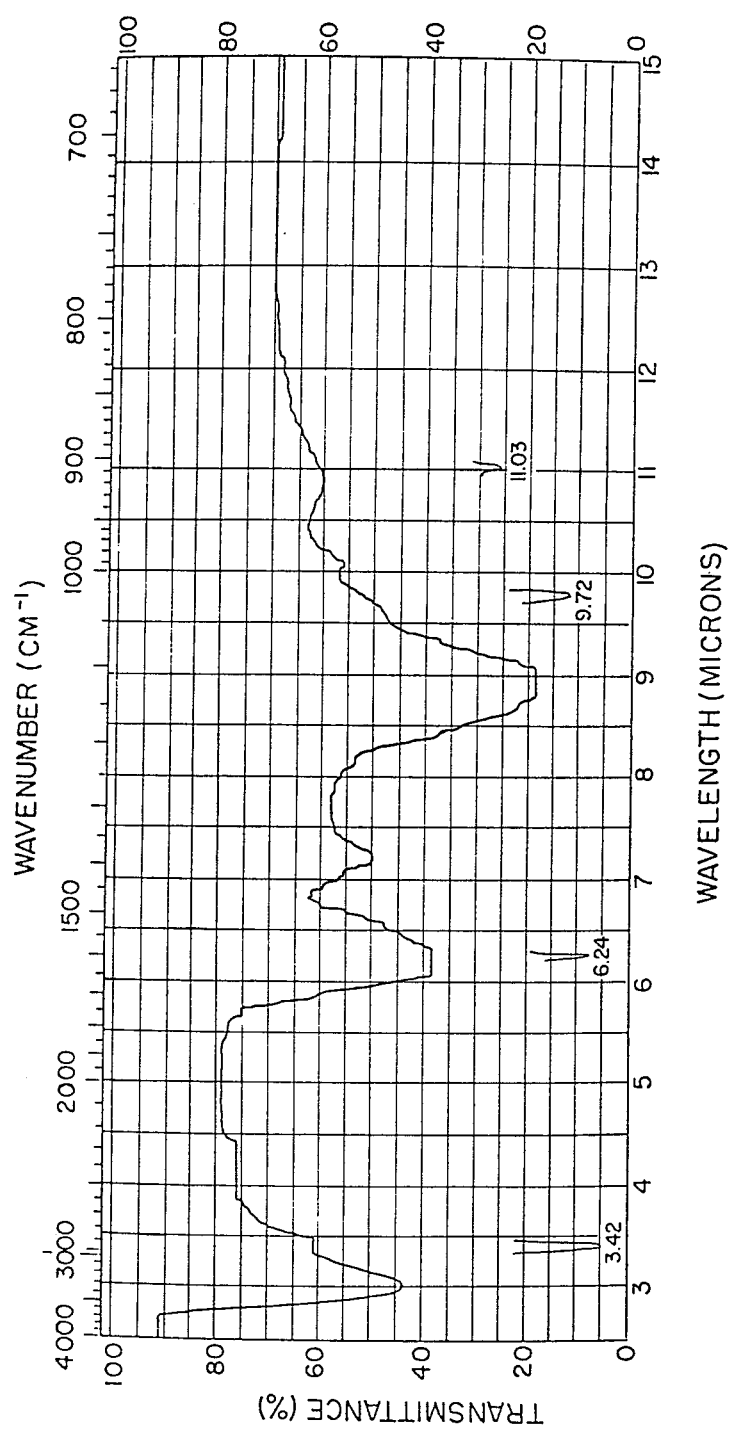
FIG. 10 is an IR of a granulocytic chalone extract (KBr) disc). The concentration was 0.5 mg of extract to 2000 mg KBr.

What is claimed is:

1. A pharmaceutical composition for producing temporary remissions with minimal serious side effects in the treatment of myeloid leukaemia in human patients in intravenous injectable form which comprises an antimyeloid leukaemic effective amount of granulocytic chalone having an elemental analysis of carbon 43.6%, hydrogen 5.8% and nitrogen 6.0%, a molecular weight less than 1.500 daltons when determined by gel techniques and having an infrared spectrum as shown in FIG. 10, sufficient to produce such remissions without impairing the immune defense system of the patient as the active therapeutic agent in combination with a pharmaceutically acceptable carrier suitable for intravenous injection to human patients.

2. A composition according to claim 1 wherein the pharmaceutically acceptable carrier is physiological saline and the concentration of chalone is 1 to 10 mg/ml.

3. A method for producing temporary remissions with minimal serious side effects in the treatment of human patients suffering from myeloid leukaemia which comprises administering by intravenous injection to a human patient suffering from myeloid leukaemia repeated doses of granulocytic chalone having an elemental analysis of carbon 43.6%, hydrogen 5.8% and nitrogen 6.0%, a molecular weight less than 1,500 daltons when determined by gel techniques and having an infrared spectrum as shown in FIG. 10, over an extended treatment period in an amount sufficient to produce such remissions without impairing the immune defense system of the patient.

4. A method according to claim 3 wherein the granulocytic chalone is dissolved in a pharmaceutically acceptable carrier suitable for intravenous injection.

5. Granulocytic chalone of sufficient purity to produce temporary remissions with minimal serious side effects in humans with myeloid leukaemia having an elemental analysis of carbon 43.6%, hydrogen 5.8%, and nitrogen 6.0%, a molecular weight less than 1,500 daltons when determined by gel techniques and having an infrared spectrum as shown in FIG. 10.

* * * * *